United States Patent [19]

Sandhu et al.

[11] Patent Number: 5,958,693
[45] Date of Patent: Sep. 28, 1999

[54] EXTRACTION OF DNA BY BOILING CELLS IN AN ALKALINE PHENOL/GUANIDINE THIOCYANATE SOLUTION

[75] Inventors: Gurpreet S. Sandhu; Bruce C. Kline, both of Rochester, Minn.

[73] Assignee: Bayer Corporation, E. Walpole, Mass.

[21] Appl. No.: 08/934,877

[22] Filed: Sep. 22, 1997

Related U.S. Application Data

[63] Continuation of application No. 08/435,684, May 5, 1995, Pat. No. 5,707,802, which is a continuation-in-part of application No. 08/373,127, Jan. 13, 1995, Pat. No. 5,763,169.

[51] Int. Cl.$^6$ .................................................. C12Q 1/68
[52] U.S. Cl. .............................................. 435/6; 536/23.1
[58] Field of Search ............................. 435/6, 220, 91.1; 536/23.1; 935/1, 19

[56] References Cited

U.S. PATENT DOCUMENTS

| | | | |
|---|---|---|---|
| 4,851,330 | 7/1989 | Kohne | 435/6 |
| 5,288,611 | 2/1994 | Kohne | 435/6 |
| 5,292,874 | 3/1994 | Milliman | 536/24.32 |
| 5,324,632 | 6/1994 | Weisburg et al. | 435/6 |
| 5,352,579 | 10/1994 | Milliman | 435/6 |
| 5,364,759 | 11/1994 | Caskey et al. | 435/6 |
| 5,407,814 | 4/1995 | Pearson et al. | 435/91.2 |
| 5,501,951 | 3/1996 | Milliman | 435/6 |
| 5,503,980 | 4/1996 | Cantor | 435/6 |
| 5,525,464 | 6/1996 | Drmanac et al. | 435/6 |
| 5,580,971 | 12/1996 | Mitsuhashi | 536/24.32 |
| 5,593,841 | 1/1997 | Hogan et al. | 435/6 |

FOREIGN PATENT DOCUMENTS

| | | | |
|---|---|---|---|
| 0272009A2 | 6/1988 | European Pat. Off. | C12Q 1/68 |
| 0327390A2 | 8/1989 | European Pat. Off. | C12N 15/00 |
| 0422872A3 | 4/1991 | European Pat. Off. | C12Q 1/68 |
| 0438587B1 | 4/1995 | European Pat. Off. | C12Q 1/68 |
| 88/03957 | 6/1988 | WIPO | C12Q 1/68 |
| 90/13669 | 11/1990 | WIPO | C12Q 1/68 |

OTHER PUBLICATIONS

G. S. Sandhu et al., "Molecular Probes for Diagnosis of Fungal Infections," Journal of Clinical Microbiology, vol. 33, No. 11, pp. 2913–2919, Nov. 1995.
P. Chomczynski and N. Sacchi, "Single–Step Method of RNA Isolation by Acid Guanidinium Thiocyanate–Phenol–Chloroform Extraction," Analytical Biochemistry, vol. 162, No. 1, pp. 156–159, Apr. 1987.
Daniel Todd et al., "Detection and Differentiation of Chicken Anemia Virus Isolates by Using the Polymerase Chain Reaction," Journal of Clinical Microbiology, vol. 30, No. 7, pp. 1661–1666, Jul. 1992.
ATCC Catalogue of Filamentous FUNGI, 18th Edition, pp. 50, 112–113 (1991).
Carr, L. G. et al., "Organization of the 5.8S, 16–18S and 23–28S ribosomal RNA genes of *Cephalosporium–acremonium*", Current Genetics, vol. 12, pp. 209–214 (1987).
Chomczynski and Sacchi, *Analytical Biochemistry*, vol. 162, pp. 156–159 (1987).
Holmes et al., *Journal of Clinical Microbiology*, vol. 32, pp. 228–231 (1994).
Hopfer et al., *Journal of Medical and Veterinary Mycology*, vol. 31, pp. 65–75 (1993).
Kwon–Chung and Bennett, *Medical Mycology*, Lee and Febiger, 1992.
Leclerc et al., *Journal of Medical and Veterinary Mycology*, vol. 32, pp. 331–341 (1994).
Lott et al., Yeast, vol. 9, pp. 1199–1206 (1993).
Maiwald et al., *Journal of Medical and Veterinary Mycology*, vol. 32, pp. 115–122 (1994).
Makimura et al., *Journal of Medical Microbiology*, vol. 40, pp. 358–364 (1994).
Mitchell et al., *Journal of Clinical Microbiology*, vol. 32, pp. 253–255 (1994).
Moukhamedov R., et al., "Use of Polymerase Chain Reaction–Amplified Ribosomal Intergenic Sequences for the Diagnosis of *Verticillium tricorpus*", Phytopathology, vol. 84, pp. 256–259 (1994).
Nakamura et al, Rinsho Byuri — Japanese Jour. of Clinical Pathology, vol. 42, pp. 676–681 (1994).
Neuvéglise C., et al., "Identification of group–I introns in the 28s rDNA of the entomopathogenic fungus *Beauveria brongniartii*", Current Genetics, vol. 27, pp. 38–45 (1994).
Sandhu, G. S., et al., "Molecular Probes for Diagnosis of Fungal Infections", Journal of Clinical Microbiology, vol. 33, pp. 2913–2919 (1995).
Sarosi and Davies, eds., Fungal Diseases of the Lung, Raven Press, 1993.
Spreadbury et al., *Journal of Clinical Microbiology*, vol. 31, pp. 615–621 (1993).
Stockman et al., *Journal of Clinical Microbiology*, vol. 31, pp. 845–850 (1993).
Vilgalys, R. et al., "Rapid Genetic Identification and Mapping of Enzymatically Amplified Ribosomal DNA from Several Cryptococcus Species", Journal of Bacteriology, vol. 172, No. 8, pp. 4238–4246 (1990).

*Primary Examiner*—Scott W. Houtteman
*Attorney, Agent, or Firm*—Arthur S. Morgenstern; Mark A. Kassel

[57] ABSTRACT

Nucleic acid probes and primers are described for detecting fungi that cause disease in humans and animals, as well as spoilage of food and beverages. These probes can detect rRNA, rDNA or polymerase chain reaction products from a majority of fungi in clinical, environmental or food samples. Nucleic acid hybridization assay probes specific for Acremonium sp., *Aspergillus clavatus, Aspergillus flavus, Aspergillus fumigatus, Aspergillus glaucus, Aspergillus nidulans, Aspergillus niger, Aspergillus ochraceus, Aspergillus terreus, Aspergillus unguis, Aspergillus ustus*, Beauveria sp., Bipolaris sp., Blastoschizomyces sp., *Blastomyces dermatitidis, Candida albicans, Candida glabrata, Candida guilliermondii, Candida kefyr, Candida krusei, Candida lusitaniae, Candida parapsilosis, Candida tropicalis*, Chrysosporium sp., Cladosporium sp., *Coccidioides immitis, Cryptococcus neoformans* var gattii serotype B, *Cryptococcus neoformans* serotype A, *Cryptococcus laurentii, Cryptococcus terreus*, Curvularia sp., Fusarium sp., *Filobasidium capsuligenum*, Filobasidiella (Cryptococcus) neoformans var bacillispora serotype C, Filobasidiella (Cryptococcus) neoformans var neoformans serotype D, *Filobasidium uniguttulatum*, Geotrichum sp., *Histoplasma capsulatum*, Malbranchea sp., Mucor sp., Paecilomyces sp., Penicillium species, *Pseudallescheria boydii*, Rhizopus sp., *Sporothrix schenkii, Scopulariopsis brevicaulis, Scopulariopsis brumpti, Saccharomyces cerevisiae*, and *Trichosporon beigelii* are also described.

8 Claims, 1 Drawing Sheet

EXTRACTION OF DNA BY BOILING CELLS IN AN ALKALINE PHENOL/GUANIDINE THIOCYANATE SOLUTION

This application is a continuation of U.S. patent application Ser. No. 08/435,684, filed May 5, 1995, now U.S. Pat. No. 5,707,802, which is a continuation-in-part of U.S. patent application Ser. No. 08/373,127, filed Jan. 13, 1995, now U.S. Pat. No. 5,763,169.

FIELD OF INVENTION

The inventions described and claimed herein relate to the design and composition of two nucleic acid probes capable of detecting many different fungal organisms in clinical, food, environmental and other samples. The inventions described and claimed herein also relate to the design and composition of probes capable of specifically detecting and identifying Acremonium sp., *Aspergillus clavatus, Aspergillus flavus, Aspergillus fumigatus, Aspergillus glaucus, Aspergillus nidulans, Aspergillus niger, Aspergillus ochraceus, Aspergillus terreus, Aspergillus unguis, Aspergillus ustus*, Beauveria sp., Bipolaris sp., Blastoschizomyces sp., *Blastomyces dermatitidis, Candida albicans, Candida glabrata, Candida guilliermondii, Candida kefyr, Candida krusei, Candida lusitaniae, Candida parapsilosis, Candida tropicalis*, Chrysosporium sp., Cladosporium sp., *Coccidioides immitis*, Cryptococcus neoformans var gattii serotype B, Cryptococcus neoformans serotpe A, *Cryptococcus laurentii, Cryptococcus terreus*, Curvularia sp., Fusarium sp., *Filobasidium capsuligenum*, Filobasidiella (Cryptococcus) neoformans var bacillispora serotype C, Filobasidiella (Cryptococcus) neoformans var neoformans serotype D, *Filobasidium uniguttulatum*, Geotrichum sp., *Histoplasma capsulatum*, Malbranchea sp., Mucor sp., Paecilomyces sp, *Penicillium species, Pseudallescheria boydii*, Rhizopus sp., *Sporothrix schenkii*, Scopulariopsis brevicaulis sp., *Scopulariopsis brumpti, Saccharomyces cerevisiae*, and *Trichosporon beigelii*. in clinical, food, environmental and other samples.

BACKGROUND OF INVENTION

Fungi are eukaryotic microorganisms that are universally distributed. While in nature fungi play a major role in the decomposition of plant materials, they are also responsible for spoilage of food, beverage and pharmaceutical preparations. Out of an estimated 100,000 species of fungi described by mycologists, approximately 150 species are pathogenic to man and animals. The increasing incidence of AIDS and the development of newer treatments for hematologic malignancies and organ transplants has lead to an increase in the number of immunocompromised patients. These patients have a high risk of developing fungal infections, which if not rapidly diagnosed and treated are capable of causing death in a matter of days. The number of antifingal drugs is limited and their toxic side effects on the patient are much higher than that of comparable antibacterial therapy. A rapid diagnosis of fingal infection and start of treatment is critical in these patients. Books by Kwon-Chung and Bennett, along with Sarosi and Davies, provide an overview into the medical importance of fungi.

Fungal organisms are identified by morphology and nutritional characteristics. Fungi may take anywhere from two days to several weeks to grow in culture and often the same organism can take radically different forms depending on the growth conditions. This makes timely identification difficult even for the classically trained expert and impedes the treatment of patients where rapid identification of genus and species is of medical advantage.

The incidence and distribution of major pathogenic fingi varies by geographic location. *Aspergillus fumigatus, Blastomyces dermatitidis, Candida albicans, Coccidiodes immitis, Cryptococcus neoformans, Histoplasma capsulatum, Paracoccidioides brasiliensis, Pseudallescheria boydii* and *Sporothrix schenkii* represent some of the leading causes of mycotic infections.

*Aspergillus fumigatus* is among the top three causes of systemic fungal infection treated in hospitals. It usually affects patients with organ transplants, acute leukemias and burns and can be rapidly fatal if not diagnosed quickly. With over 150 species of Aspergillus present in the soil, air and water, accurate detection of *Aspergillus fumigatus* becomes extremely important *Aspergillus clavatus, Aspergillus flavus, Aspergillus fumigatus, Aspersillus glaucus, Aspergillus nidulans, Aspergillus niger, Aspergillus ochraceus, Aspergillus terreus, Aspergillus unguis* and *Aspergillus ustus* represent a majority of Aspergillus species seen in clinical specimens and their presence can cause diagnostic difficulties. *Aspergillus flavus, Aspergillus fumigatus* and *Aspergillus niger* have been linked with disease in humans, with *Aspergillus fumigatus* being the predominant pathogen in North America. A few immunologic tests exist for *Aspergillus fumigatus* but these have limited sensitivity and specifcity. There are also reports of development of polymerase chain reaction based tests for *Aspergillus fumigatus* based on the amplification of the *Asp fl* antigen gene and a ribosomal intergenic spacer (Spreadbury et. al.). The Spreadbury technique is based on the PCR amplification of a 401 bp fragment spanning the large subunit rRNA/intergenic spacer region. This relies on a pair of primers to specifically amplify DNA from *Aspergillus fumigatus* only, and is of no utility in identifying other fungi.

*Blastomyces dermatitidis* is present in the soil, usually in bird droppings and animal feces. Infections often occur at construction sites and the ensuing lung infiltration and pneumonitis are usually fatal in immunocompromised patients. Diagnosis by culture may take weeks, and the organism is occasionally mistaken for other fungi. Existing immunological diagnostic tests are unreliable, and there is a need for rapid and reliable DNA based diagnostic tests. Similarly, *Histoplasma capsulatum* exists in the soil and is known to have infected at least 20% of the population of North Amerca. Most infections start in the lung and resolve spontaneously, but may occasionally spread to other organs. AIDS patients represent a growing number of cases of Histoplasmosis. Diagnosis is difficult as immunological tests are often negative during the first 4–6 weeks of infection. *Coccidioides immitis* is found in abundance in the soil in Southwestern United States. Dust storms, farming building construction, earthquakes and even hiking have been linked with outbreaks of disease. Lung infection followed by cavitation and disseminated miliary coccidioidomycosis are seen. Meningitis is usually lethal, and as with other fungi, mortality is highest in debilitated hosts. Four serotypes of *Cryptococcus neoformans* cause disease in humans. These are Cryptococcus neoformans serotype A, Cryprococcus neoformans var gatti serotype B, Filobasidiella (Cryptococcus) neoformans var bacillispora serotype C and Filobasidiella (Cryptococcus) neoformans var. neoformans serotype D. The incidence of this disease is growing rapidly, with up to 10% of HIV infected people developing cryptococcosis. DNA probes capable of detecting all 4 serotpes are required for the early diagnosis and treatment for life threatening infections like cryptococcal meningitis. A report by Stockman et. al. discusses commercial tests for Histoplasma, Blastomyces, Coccidioides, and Cryptococcus based on the 18S rRNA (Gen-Probe, Inc., San Diego, Calif.). The authors report sensitivities ranging from 87.8 to 100% and a specificity of 100%. One drawback of these probes is that these are used on rRNA extacted from fungal cultures. As some fungi may require up to 3 weeks to grow in culture, thiis technique cannot be used to expedite diagnosis until a culture becomes available.

*Candid albicans* is one of the most common causes of fungal infection in humans. It is present in the respiratory, gastrointestinal and female genital tract of healthy individuals, and acts as an opportunistic pathogen in debilitated individuals on steroid or chemotherapy. Diabetes mellitus and indwelling catheters are other predisposing causes. Immunocomprormised hosts show rapid hemtogenous spread of fungi. Morbidity and mortality in untreated cases is high. *Candida glabrata, Candida guilliermondii, Candida keyfr, Candida krusei, Candida lusitaniae, Candida parapsilosis* and *Candida tropicalis* are also known to cause disease in humans. DNA probes capable of identifying these individual species would eliminate the need for multiple blood cultures and lengthy biochemical seciation.

Recent advances in molecular techniques have led to the approach of microbe detection and identification based upon the DNA sequence of ribosomal genes. Commonly used detection techniques include either direct amplification of the ribosomal DNA (rDNA) genes by the polymense chain reaction, or reverse transription of the ribosomal RNA (rRNA) into complementary DNA (cDNA) followed by polymerase chain reaction amplification of the cDNA. Ribosomes are composites of unique rRNA and protein species that function in the translation of messenger RNA into protein. Evolutionary studies are consistent with the interpretation that all extant life has evolved from a single organism. Thus, all cellular organisms contain rRNA and these rRNAs are related by evolution. The evolutionary process is such that each species of organism appears to have unique regions of sequence in its ribosomal genes. The presence of these unique species specific regions allows one to design DNA probes that under conditions of hybridization will specifically bind to, and identify the polymerase chain reaction amplified DNA from only one species of fungus. For the purposes of this application, the word "primer" is used to mean a nucleotide sequence which can be extended by template-directed polymerization, and "probe" is used to mean a nucleotide sequence capable of detecting its complementary sequence by hybridization. Also, for the purpose of this application, the phrase "nucleotide sequence" is intended to include either DNA or RNA forms or modification thereof. Furthermore, those versed in the art will recognize that primer sequences can be used as probes and vice versa. The use of nucleic acid hybridization to detect specific nucleic acid sequences of interest is also described by Kohne (U.S. Pat. No. 4,851,330, 7/1989).

In prokaryotes and eukaryotes, ribosomal RNA and the corresponding rDNA genes are identified by the size of the RNA. The sizes are related in terms of sedimentation velocity or S values. Thus, for prokaryotes the values are 5S, 16S, and 23S; and for eukaryotes the values are 5S, 5.8S, 18S and 28S. Because all ribosomes perform the same function which is essential for cell viability, ribosomal sequences are largely conserved, yet certain regions of each ribosomal species are subject to more variation without consequence to function. It is these hypervariable regions that allow one to identify different species amongst members of the same genus. As noted in the references, there are several reports where 5S, 18S and the intergenic spacer between 5.8S and 28S rDNA have been used for the detection and identification of fungi (Holmes et. al., Hopfer et. al., Lott et. al., Maiwald et. al., Makimura et. al., Mitchell et. al., Nakamura et. al.). Holmes et. al. describe a PCR test based on the co-amplification of the 5S rDNA and an adjacent nontranscribed spacer region. This identifies only *Candida albicans* and detects other Candida species without identifying individual organisms. Hopfer et. al. and Maiwald et. al. both use universal primers to amplify 18S rDNA from several fungi including Candida sp., *Aspergillus fumigatus, Cryptococcus neoformans* and *Trichosporon sp.* These amplicons are digested with restriction enzymes and the cut fragments are sized by gel electrophoresis. This restriction fragment length polymorphism pattern enables them to identify most but not all organisms. This technique can be used on amplified DNA from a pure fungal culture. As clinical samples such as sputum usually contain multiple fungal organisms, this technique has little utility in diagnosis as multiple overlapping fragments obtained from a mix of fungi would be nearly impossible to interpret. Lott et. al. use the 5.8S RNA and the internal transcribed spacer (ITS2) to identify and speciate *Candida albicans* and related Candida species. Makimura amplifies a 687 bp fragment from the 18S rDNA of 25 medically important fungi and uses these in the diagnosis of *Candida albicans* in clinical samples. Mitchell uses nested PCR to amplify 5.8S and internal transcribed spacer (ITS) to identify *Cryptococcus neoformans*. No subsequent testing is done to verify the identity of the amplified DNA. Nakamura et. al. use 18S primers to detect *Aspergillus fumigatus* infections of the lung. Most protocols given in these references can only be used to detect an extremely limited number of fungi from a clinical specimen. Hopfer et. al. and Maiwald et. al. can identify multiple organisms from pure cultures, but their utility for clinical specimens containing multiple fungal species is limited at best.

United States patents have been issued to Weisburg et. al. for probes developed for the detection of 18S small subunit ribosomal RNA sequences in fungi. These probes will detect fungi from many species, but cannot be used easily to identify any single species. United States patents have also been issued to Milliman for probes developed for the specific detection of the bacteria Staphylococcus aureus based on the 16S ribosomal sequences. Hogan et. al. (European Pat. App. 0,272,009) describe one fungal probe for 18S rRNA and three fungal probes for 28S rRNA sequences. Two of these 28S probes detect several different fungi while the third probe detects *Candida krusei* from a limited panel of 10 fungi. None of the 28S probes described by Hogan et. al. is related to any of the probes described in our invention. All probes claimed in our invention can be mapped within the first 900 base pairs of a 28S gene. The probes described by Hogan et. al. are located further 3' on the 28S sequence, between base pairs 1000 and 2000 (these numbers are comparable to the primary sequence of *Saccharomyces cerevisiae* 28S rRNA gene. Genbank accession number: J01355). Leclerc et. al. have published reports analyzing the phylogenetic relationship between fungi based on partial DNA sequences of several fungal 28S genes sequenced by them. Some of the organisms claimed to have been sequenced by Leclerc are the same as some organisms sequenced by us. These are *Sporothrix schenckii, Pseudallescheria boydii, Blastomyces dermatitidis, Histoplasma capsulatum* and Chrysosporium sp. Leclerc et. al. have not published any sequence data in their report, and to the best of our knowledge, they have not made these sequences publically available. The reverse-complement sequence of their sequencing primer 401 (TCCCTTTCAA CAATTTCACG) overlaps our SEQ ID NO: 1 (GTGAAATTGT TGAAAGGGAA) by 19 nucleotides and their sequencing primer 636 (GGTCCGTGTT TCAAGACGG) overlaps our SEQ ID NO: 2 (GACTCCTTGG TCCGTGTT) by 10 nucleotides. We are aware of no reports in the literature of variable regions from 28S rRNA genes of fungi being used as targets for the development of species specific diagnostic probes.

As discussed above, most present techniques for the molecular detection of fungi rely on the use of highly specific primers for the PCR amplification of only one fungal species. Those that employ "Universal" primers for a PCR amplification of DNA from multiple organisms, use post-PCR amplicon identification techniques that are useful only on pure cultures of fungi. These are not be able to identify fungi from a clinical specimen containing multiple fingal organisms. Our first aim was to develop "Universal" primers for the 28S gene. These primers would be capable of amplifying in a PCR, 28S rDNA from most fungi. Our subsequent aim was to develop species specific probes for fungi of interest, that would be used to analyze our "Universal" 28S amplicon. These species specific probes would be able to detect the presence of fungi of interest even in situations containing mixed fungal species.

One aspect of this invention is to provide nucleic acid primers capable of detecting 28S sequences from DNA or RNA of most fungi. These would be used as "Universal" primers in a polymerase chain reaction to amplify 28S sequences from any fungus present in clinical, food, environmental or other samples. These "Universal" primers would also be used to sequence the amplified DNA. The sequence obtained would be used to identify the fungus by comparing with a database of known fungal sequences.

A second aspect of this invention is to provide nucleic acid probes capable of detecting and identifying, by nucleic acid hybridization, the pathogens Aspergillus fumigatus, Blastomyces dermatitidis, Candida albicans, Coccidioides immitis, Cryptococcus neoformans, Histoplasma capsulatum, Aspergillus flavus, Aspergillus glaucus, Aspergillus niger, Aspergillus terreus, Candida glabrata, Candida guilliermondii, Candida kefyr, Candida krusei, Candida lusitaniae, Candida parapsilosis, Candida tropicalis, Pseudallescheria boydii, Sporothrix schenckii and other species by use of any of several different formats. Additionally, nucleotide sequence information is provided to identify these pathogens and other fungi by DNA sequence comparison (FIG. 2) or by the construction of additional probes.

SUMMARY OF THE INVENTION

Nucleic acid probes and primers are described for detecting fungi that cause disease in humans and animals, as well as spoilage of food and beverages. These probes can detect rRNA, rDNA or polymerase chain reaction products from a majority of fungi in clinical, environmental or food samples. Nucleic acid hybridization assay probes specific for Aspergillus fumigatus, Blastomyces dermatitidis, Candida albicans, Coccidioides immitis, Cryptococcus neoformans, Histoplasma capsulatum, Aspergillus flavus, Aspergillus glaucus, Aspergillus niger, Aspergillus terreus, Candida glabrata Candida guilliermondii, Candida kefyr, Candida krusei, Candida lusitaniae, Candida parapsilosis, Candida tropicalis, Pseudallescheria boydii, Sporothrix schenckii and other species (Table 1 and FIG. 2) are also described.

DETAILS OF THE INVENTION

Figure 1:
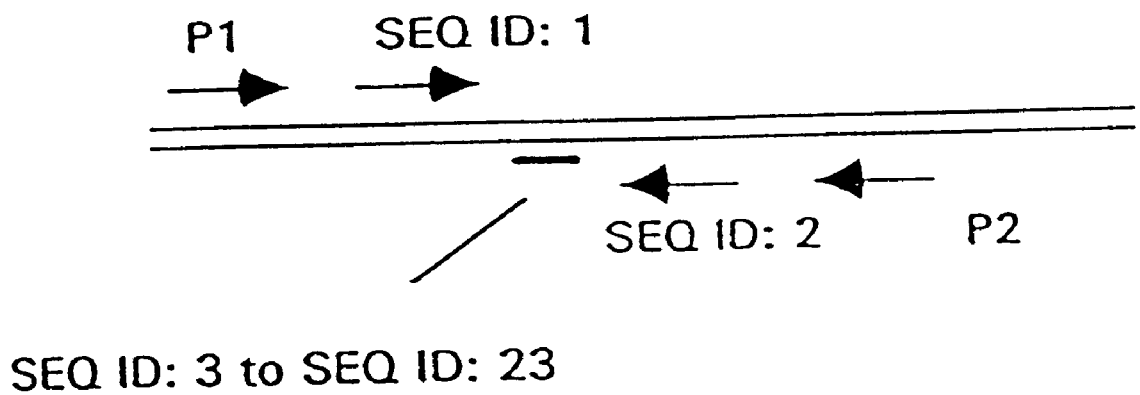
FIG. 1 represents the relative position of the sequences described on the 28S subunit of fungi.

Our first objective was to develop nucleic acid primers for use in a polymerase chain reaction to amplify 28S genes from all fungi likely to be present in a clinical sample. This amplified DNA would then be amenable to probing with several different species specific probes. Each one of these species specific probes would, under conditions of hybridization, anneal to 28S ribosomal DNA from only one species of fungus, thereby detecting and identifying the species of fungus present in the clinical sample. The 28S gene was selected as a target because it had regions that were conserved among fungi and these would provide potential annealing sites for "universal" fungal probes. The ribosomal 28S genes were also expected to have hypervariable regions that would be unique enough to provide sites for species specific probes. The large rRNA gene is called the 23S rRNA gene in prokaryotes and 28S in eukaryotes. This designation is based on the length and therefore the sedimentation coefficient of these rRNA molecules. Fungal large subunit rRNAs vary in size among different organisms and are often referred to as being 25S, 26S or 28S. Since fungi are eukaryotes, and to maintain uniformity in this application, we shall refer to fungal large subunit rRNA as 28S rRNA.

Published sequences from Cryptococcus neoformans, two Candida albicans, Saccharomyces cerevisiae and two Schizosaccharomyces pombe 28S genes are approximately 3.5 kilobases in length (Genbank accession numbers: L14068, L28817, X70659, J01355, Z19136 & Z19578). These four sequences were aligned, and a region of sequence variability was found clustered between coordinates 200 and 700 from the 5' end of these genes. As an initial starting point, two nucleic acid primers P1 (ATCAATAAGC GGAGGAAAAG)(SEQ ID NO:75) and P2 (CTCTGGCTTC ACCCTATTC)(SEQ ID NO:76)(see FIG. 1), capable of hybridizing to all 4 of the above mentioned organisms and not to human 28S sequences (GenBank accession number: M11167), were designed and used under low stringency hybridization conditions in a polymerase chain reaction to amplify approximately 800 base pairs of DNA spanning this hypervariable region from the following 34 fungi that were obtained from the Mayo Clinic fungal collection: Acremonium sp., Aspergillus clavatus, Aspergillus fumigatus, Aspergillus glaucus, Aspergillus nidulans, Aspergillus niger, Aspergillus ochraceus, Aspergillus terreus, Aspergillus unguis, Aspergillus ustus, Beauvaria sp., Bipolaris sp., Blastomyces dermatitidis, Candida albicans, Candida glabrata, Candida guilliermondii, Candida kefyr, Candida krusei, Candida lusitaniae, Candida parapsilosis, Candida tropicalis, Chrysosporium sp., Cladosporium sp., Coccidioides immitis, Cryptococcus neoformans serotype A, Curvularia sp., Geotrichum sp., Histoplasma capsulatum, Mucor sp., Penicillium sp., Pseudallescheria boydii, Saccharomyces cerevisiae, Sporothrix schenkii and Trichosporon beigelii.

DNA was extracted from the fungi listed above by the following method. A loopful of fungal culture was scraped off a culture plate using a sterile inoculation loop. The fungus was added one milliliter of sterile water in a 1.5 ml Sarsted (Newton, N.C.) screw cap microcentrifuge tube. This tube was placed in a boiling water bath for 20 minutes in order to lyse the fungus and release DNA from the cells. Two microliters of this whole cell lysate was used in a PCR to amplify 28S rDNA. All PCR amplifications were carried out as hot-start reactions in a 50 ul reaction volume using Perkin-Elmer (Norwalk, Conn.) 0.5 ml thin-wall polypropylene tubes and a Perkin-Elmer thermal cycler. Reagents added to the tube initially were 2.5 ul of 10× PCR buffer (100 mM tris pH 8.3, 500 mM KCl, 15 mM $MgCl_2$), 5.0 ul of 50% glycerol/1 mM cresol red, 8.0 ul of dNTP mix (1.25 mM each of dATP, dGTP, dTTP and dCTP), 12 picomoles of each nucleic acid primer and sterile water to make up a volume of 25 ul. A wax bead (Ampliwax Gem-100, Perkin-Elmer) was added and the tubes heated to 77° C. for 1 minute and cooled to room temperature to form a wax barrier. 2.5 ul of 10× PCR buffer, 5.0 ul of 50% glycerol/1 mM cresol red, 0.2 ul Taq polymerase (AmpliTaq 5U/ul, Perkin-Elmer) and 15.3 ul of sterile water was added to the tube along with 2.0 ul of DNA from the fungal whole cell lysate described above. 50 cycles of thermal cycling was carried out at 94° C.—30 sec, 40° C.—1 min, 72° C.—2 min. The amplified DNA was electrophoresed and purified from a low melt agarose gel by tris buffered phenol pH 8.0, phenol/chloroform/isoamyl alcohol (25:24:1 by vol.) and 3 ether extractions, followed by isopropanol precipitation and 70% ethanol wash.

We completely sequenced both strands of DNA amplified from the organisms listed above. All sequencing was carried out on an Applied Biosystems 373A sequencer. Every nucleotide in the sequences generated was verified and confirmed by examining the complementary nucleotide from the second strand sequence. We had now created a novel database consisting of nucleic acid sequences spanning a variable region of the 28S rDNA from a diverse collection of medically important fungi.

While the complete sequences for *Candida albicans, Cryptococcus neoformans* and *Saccharomyces cerevisiae* 28S genes had previously been published and deposited in GenBank, it was not obvious, nor had it been defined, whether any regions of sequence identity among these three organisms would also be conserved among all fungi of interest. DNA sequences from all the fungi in our novel 28S database had to be analyzed in order to develop "Universal" 28S probes. All sequences were subjected to extensive manipulation to identify optimal relative allignments in order to identify regions of similarity for use as "Universal" probes. The selected probe sequences had to meet several important criteria besides the condition of being present in 28S genes from most fungal species. Each probe sequence required an appropriate thermal profile, secondary structure and utility in a DNA amplification reaction. These probes were optimized to work for PCR amplification in pure cultures of fungus, as well as in the presence of DNA from multiple sources as in the case of clinical specimens. The probes were also designed to facilitate direct sequencing of the amplified DNA. Our analysis led to the discovery of the oligonucleotide probes listed in (SEQ ID NO:1) and (SEQ ID NO:2). (For their location, see FIG. 1.) The successful identification of these two probes ((SEQ ID NO:1) and (SEQ ID NO:2)) completed our first objective to develop nucleic acid probes that would hybridize to, and detect 28S rRNA and rDNA from a majority of fungi (FIG. 1 and Table 1). As shown later in this application, the novel sequence information generated by the use of our "Universal" probes allowed us to develop species-specific probes ((SEQ ID NO:3) to (SEQ ID NO:23)) capable of identifying 19 different disease-causing fungi.

TABLE 1

Presence of hybridization sites for probes SEQ ID NO: 1 and SEQ ID NO: 2 in 28S nucleic acid sequences.

|  | SEQ ID NO: 1 | SEQ ID NO: 2 |
| --- | --- | --- |
| *Acremonium sp.* | + | + |
| *Aspergillus clavatus* | + | + |
| *Aspergillus flavus* | + | + |
| *Aspergillus fumigatus* | + | + |
| *Aspergillus glaucus* | + | + |
| *Aspergillus nidulans* | + | + |
| *Aspergillus niger* | + | + |
| *Aspergillus ochraceus* | + | + |
| *Aspergillus terreus* | + | + |
| *Aspergillus unguis* | + | + |
| *Aspergillus ustus* | + | + |
| *Beauvaria sp.* | + | + |
| *Bipolaris sp.* | + | + |
| *Blastomyces dermatitidis* | + | + |
| *Blastoschizomyces sp.* | + | + |
| *Candida albicans* | + | + |
| *Candida glabrata* | + | + |
| *Candida guilliermondii* | + | + |
| *Candida kefyr* | + | + |
| *Candida krusei* | + | + |
| *Candida lusitaniae* | + | + |
| *Candida parapsilosis* | + | + |
| *Candiaa tropicalis* | + | + |
| *Chrysosporium sp.* | + | + |
| *Cladosporium sp.* | + | + |
| *Coccidioides immitis* | + | + |
| *Ctyptococcus laurentii* | + | + |
| *Cryptococcus neoformans* serotype A | + | + |
| *Cryptococcus neoformans* var. gattii serotype B | + | + |
| *Curvularia sp.* | + | + |
| *Filobasidiella* (Cryptococcus) *neoformans* var bacillispora serotype C | + | + |
| *Filobasidiella* (Cryptococcus) *neoformans* var neoformans serotype D | + | + |
| *Filobasidium capsuligenium* | + | + |
| *Filobasidium uniguttulatum* | + | + |
| *Fusarium sp.* | + | + |
| *Geotrichum sp.* | + | + |
| *Histoplasma capsulatum* | + | + |
| *Malbranchea sp.* | + | + |
| *Mucor sp.* | + | + |
| *Paecilomyces sp.* | + | + |
| *Penicillium sp.* | + | + |
| *Pseudallescheria boydii* | + | + |
| *Rhizopus sp.* | + | + |
| *Saccharomyces cerevisiae* | + | + |
| *Scopulariopsis brevicaulis* | + | + |
| *Scopulariopsis brumptii* | + | + |
| *Sporothrix schenckii* | + | + |
| *Trichosporon beigelii* | + | + |
| Human | − | + |

Probes SEQ ID NO: 1 and SEQ ID NO: 2 were used to successfully amplify (Table 2) and sequence DNA (FIG. 2) spanning this variable region from the following 49 organisms: Acremonium sp., *Aspergillus clavatus, Aspergillus flavus, Aspergillus fumigatus, Aspergillus glaucus, Aspergillus nidulans, Aspergillus niger, Aspergillus ochraceus, Aspergillus terreus, Aspergillus unguis, Aspergillus ustus,* Beauvaria sp., Bipolaris sp., *Blastomyces dermatitidis,* Blastoschizomyces sp., *Candida albicans, Candida glabrata, Candida guilliermondii, Candida kefyr, Candida krusei, Candida lusitaniae, Candida parapsilosis, Candida tropicalis,* Chrysosporium sp., Cladosporium sp., *Coccidioides immitis,* Cryptococcus neoformans serotype A, Cryptococcus neoformans var. gattii serotype B, Cryptococcus terreus, *Cryptococcus laurentii*, Curvularia sp., Filobasidiella (Cryptococcus) neoformans var bacillispora serotype C, Filobasidiella (Cryptococcus) neoformans var neoformans serotype D, *Filobasidium capsuligenum, Filobasidium uniguttulatum*, Fusarium sp., Geotrichum sp., *Histoplasma capsulatum*, Malbranchea sp., Mucor sp., Paecilomyces sp., Penicillium sp., *Pseudallescheria boydii*, Rhizopus sp., *Saccharomyces cerevisiae, Scopulariopsis brevicaulis, Scopulariopsis brumptii, Sporothrix schenkii* and *Trichosporon beigelii*. This list contains all 4 serotypes (A, B, C and D) of *Cryptococcus neoformans*. This sequence information generated by the use of probes SEQ ID NO: 1 and SEQ ID NO: 2 expanded the size of our database consisting of fungal 28S sequences. All amplified DNA was sequenced across both strands from a minimum of two different isolates of each organism to ensure accuracy of the data generated.

TABLE 2

Polymerase chain reaction amplification of 28S rDNA with probes SEQ ID NO: 1 and SEQ ID NO: 2.

| | PCR with SEQ ID NO: 1 & NO: 2 |
|---|---|
| *Acremonium sp.* | + |
| *Aspergillus clavatus* | + |
| *Aspergillus flavus* | + |
| *Aspergillus fumigatus* | + |
| *Aspergillus glaucus* | + |
| *Aspergillus nidulans* | + |
| *Aspergillus niger* | + |
| *Aspergillus ochraceus* | + |
| *Aspergillus terreus* | + |
| *Aspergillus unguis* | + |
| *Aspergillus ustus* | + |
| *Beauvaria sp.* | + |
| *Bipolaris sp.* | + |
| *Blastomyces dermatitidis* | + |
| *Blastoschizomyces sp.* | + |
| *Candida albicans* | + |
| *Candida glabrata* | + |
| *Candida guilliermondii* | + |
| *Candida kefyr* | + |
| *Candida krusei* | + |
| *Candida krusei* | + |
| *Candida lusitaniae* | + |
| *Candida parapsilosis* | + |
| *Candida tropicalis* | + |
| *Chrysosponum sp.* | + |
| *Cladosporium sp.* | + |
| *Coccidioides immitis* | + |
| *Cryptococcus laurentii* | + |
| *Cryptococcus neoformans serotype A* | + |
| *Cryptococcus neoformans var. gattii serotype B* | + |
| *Cryptococcus terreus* | + |
| *Curvularia sp.* | + |
| *Fiolbasidiella (Cryptococcus) neoformans var bacillispora serotype C* | + |
| *Filobasidiella (Cryptococcus) neoformans var neoformans serotype D* | + |
| *Filobasidium capsuligenum* | + |
| *Filobasidium uniguttulatum* | + |
| *Fusarium sp.* | + |
| *Geotrichum sp.* | + |
| *Histoplasma capsulatum* | + |
| *Malbranchea sp.* | + |
| *Mucor sp.* | + |
| *Paecilomyces sp.* | + |
| *Penicillium sp.* | + |
| *Pseudallescheria boydii* | + |
| *Rhizopus sp.* | + |
| *Saccharomyces cerevisiae* | + |
| *Scopulariopsis brevicaulis* | + |

TABLE 2-continued

Polymerase chain reaction amplification of 28S rDNA with probes SEQ ID NO: 1 and SEQ ID NO: 2.

| | PCR with SEQ ID NO: 1 & NO: 2 |
|---|---|
| *Scopulariopsis brumptii* | + |
| *Sporothrix schenckii* | + |
| *Trichosporon beigelii* | + |
| Human | − |

This list of fungi sequenced by us represents organisms responsible for most cases of subcutaneous and deep mycotic infections in humans and also includes saprophytes (non-pathogenic fungi) commonly encountered in clinical isolates. Since the two probes (SEQ ID NO: 1 and SEQ ID NO: 2) hybridize to 28S rDNA from all the fungi listed above, they are capable of diagnosing the presence of a majority of fungi that are likely to be present in a clinical specimen. They are believed to be primers for universally detecting fungi.

Probes listed in SEQ ID NO: 1 and SEQ ID NO: 2 were also checked for their potential ability to hybridize to, and amplify (in a polymerase chain reaction) 23S sequences from bacteria by searching for hybridization sites among the 539 bacterial 23S genes listed in GenBank. Bacterial 23S rDNAs do not have suitable hybridization sites for SEQ ID NO: 1 and SEQ ID NO: 2 and these two probes should not be able to amplify bacterial DNA under stringent conditions.

Our second objective was to develop species specific probes, which under hybridization conditions, would detect *Aspergillus fumigatus, Blastomyces dermatitidis, Candida albicans, Coccidioides immitis, Cryptococcus neoformans, Histoplasma capsulatum, Aspergillus flavus, Aspergillus glaucus, Aspergillus niger, Aspergillus terreus, Candida glabrata, Candida guilliermondii, Candida kefyr, Candida krusei, Candida lusitaniae, Candida parapsilosis, Candida tropicalis, Pseudallescheria boydii*, and *Sporothrix schenckii*. We used our database of fungal 28S nucleic acid sequences to create a multiple sequence alignment of all the organisms that we had sequenced. Every individual sequence was subjected to intensive comparison with all other sequences in our database in order to discover unique regions of sequence that would be present only in the fungus of interest, and would be absent in all other fungi. When unique stretches of sequence were identified, these were further analyzed for thermal profile and secondary structure. Each probe constructed by us will, under conditions of hybridization, specifically hybridize to and detect, nucleic acid sequence from the unique region of only one specific target fungus. Those versed in the art will recognize that specification of a single-stranded DNA sequence implies the utility of the complementary DNA sequence, as well as the two equivalent RNA sequences. Furthermore, sequences incorporating modification of any of the moieties comprising the nucleic acid (i.e., the base, the sugar or the backbone) are functional equivalents of the sequence. It should also be recognized that these additional sequences can potentially serve as probes or primers. Finally, those versed in the art recognize that comparisons of extensive DNA sequences provides enough variability and uniqueness to speciate organisms (FIG. 2).

The nucleic acid sequences for these species specific synthetic probes are listed in SEQ ID NO: 3 to SEQ ID NO: 23 There are two probes specific for *Cryptococcus*

*neoformans*, two probes specific for *Sporothrix schenckii*, and one probe each for *Aspergillus fumigatus, Blastomyces dermatitidis, Candida albicans, Coccidioides immitis, Histoplasma capsulatum, Aspergillus flavus, Aspergillus glaucus, Aspergillus niger, Aspergillus terreus, Candida glabrata, Candida guilliermondii, Candida kefyr, Candida krusei, Candida lusitaniae, Candida parapsilosis, Candida tropicalis* and *Pseudallescheria boydii* 28S rRNA and rDNA. (See Tables 3–6 and further discussion below.)

All species specific probes developed by us are novel and to the best of our knowledge have not been reported in the literature. While all 28S genes sequenced by us had several regions that were different among the various species analyzed, the regions that would function best as species specific probes under conditions of hybridization were not obvious. Extensive analysis of each 28S sequence yielded several potential probe sites. These were studied in detail to enable the selection of optimal unique sites for each probe, based on the need to obtain optimal hybridization characteristics under the test conditions. The highly specific hybridization characteristics of all probe sequences developed by us were then validated by experimental results. The prior existence in GenBank of sequences for *Candida albicans* and serotypes A and B (GenBank accession numbers L14067 and L14068) of *Cryptococcus neoformans* 28S genes was in itself not sufficient to enable even an individual versed in this field to develop specific probes for either of these two organisms. We had to obtain novel 28S sequence from *Candida albicans, Candida glabrata, Candida guilliermondii, Candida kefyr, Candida krusei, Candida lusitaniae, Candida parapsilosis, Candida tropicalis*, Cryptococcus neoformans serotype A, Cryptococcus neoformans var. gatii serotype B, *Cryptococcus terreus, Cryptococcus laurentii*, Filobasidiella (Cryptococcus) neoformans var bacillispora serotype C, Filobasidiella (Cryptococcus) neoforntans var neoformans serotype D, *Filobasidium capsuligenum* and *Filobasidium uniguttulatum* before we were able to identify potential regions for the development of species specific probes for these two fungal organisms that would not cross react with the others listed above.

Our modification of the Chomczynski technique (see Example 2, below) allows us obtain DNA from any clinical specimen, irrespective of source (see Table 8 for a variety of clinical specimens tested), within a 3 hour period. The PCR amplification and subsequent probing can be accomplished with ease within a 24 hour period. The fmal identification is therefore possible in a day as opposed to several days or weeks required by traditional methods. This speed and sensitivity of diagnosis can make a difference between life and death in debilitated patients battling fungal diseases of undetermined cause. Rapid diagnosis will allow physicians to immediately direct their therapy towards curing the identified causative fungus, rather than wait for days or weeks while the patient succumbs to an unknown fungus.

Our probes have the ability to pick out the correct target organism even in a mixed fungal infection because of their high level of specificity. The methods of Hopfer et. al. and Maiwald et. al., do not allow identification of individual species in a mixed fungal infection because restriction fragment length polymorphism results are nearly impossible to interpret when multiple organisms contribute to the restriction fragments. Their method can therefore only be used on a pure culture, and this also does not save any diagnostic time, because the fungus first has to be grown in culture.

The probes developed by us allow rapid species identification of a large number of pathogenic fungi by using multiple probes against only one PCR amplified fragment of DNA. Coupled with our modified DNA extraction technique and our ability to accurately diagnose in the case of mixed organisms, this strategy can provide the greatest amount of diagnostic information in the shortest amount of timne. This diagnostic strategy is also amenable to automation, which can result in even greater savings in time, money and effort.

The sequences and the complement of the sequences claimed in this disclosure, along with any modifications to these sequences, may potentially be utilized in assays for the identification of fungi based on several existing methodologies, as well as future improvements and alterations of this technology. These techniques include, but are not limited to, assays based on hybridization, ligation, polymerization, depolymerization, sequencing, chemical degradation, enzymatic digestion, electrophoresis, chromatography and amplification. Furthermore, all such variations ultimately are based in some selection or amplification process, some ligand or some nucleic acid moiety that recognizes or utilizes the sequences (SEQ ID NO: 1) to (SEQ ID NO:23) claimed in this application. Such variations include but are not limited to use of a variety of linear or exponential target amplification schemes, such as, any of the myriad forms of PCR, the ligase chain reaction, Q-beta repliase, etc.; direct detection of species-specific nucleic acid purified or extracted from pure fungal culture using a probe selected from the group (SEQ ID NO: 3) to (SEQ ID NO: 23); use of the complementary DNA forms of (SEQ ID NO:1) to (SEQ ID NO:23); use of the RNA forms of these sequences and their complements; and use of derivatives of these DNA or RNA sequences by the addition of one or more reporter moieties from a variety of labels including nucleic acid sequences, proteins, signal generating ligands such as acridinium esters, and/or paramagnetic particles. These techniques may be utilized with DNA, RNA or modified derivatives used as either the target or the detection molecule.

In addition to the 23 sequences SEQ ID NO: 1 to SEQ ID NO: 23, we also describe an additional 51 sequences SEQ ID NO: 24 to SEQ ID NO: 74. These 51 sequences are inclusive of SEQ ID NO: 3 to SEQ ID NO: 23 and are shown as a multiple sequence alignment (FIG. 2) with coordinate 1 corresponding to base #431 of a reference *S. cerevisiae* 28S rRNA gene. (The numbers are comparable to the primary sequence of *S. cerevisiae* 28S rRNA gene. Genbank accession number: J01355). These sequences were obtained by amplifing and sequencing 28S rDNA from various fuingi with primers SEQ ID NO: 1 and SEQ ID NO: 2. (SEQ ID NO: 1 corresponds to coordinates 403–422 and the SEQ ID NO: 2 corresponds to coordinates 645–662 of the reference *S. cerevisiae* gene).

An analysis of these aligned sequences enabled us to develop the species specific probes SEQ ID NO: 3 to SEQ ID NO: 23, and sites for these probes are shown underlined. These 51 aligned sequences contain sufficient variability, to enable a person versed in this art, to develop additional species specific hybridization probes in the 10–50 nucleotide length. Similarly, longer species specific hybridization probes encompassing the entire 200+ nucleotide length can also be envisioned. Species identification may also be accomplished by direct DNA sequence determination of any DNA amplified with primers SEQ ID NO: 1 and SEQ ID NO: 2. If the derived sequence matches approximately 98% or more of any sequence in SEQ ID NO: 24 to SEQ ID NO: 74, then the identity of the organism can be ascertained. Additionally, we recognize that parts of SEQ ID NO: 24 to SEQ ID NO: 74 may be specific for groups of fungi arranged phylogenetically at the level of genus or higher. SEQ ID NO: 24 to SEQ ID NO: 74, their complements, along with any modification to these sequences may also potentially be utilized in assays for the identification of fungi based on existing methodologies and future technologies as noted above for SEQ ID NO: 1 to SEQ ID NO: 23.

Figure 2

```
            1                                                                    70
{Rhizo2}   AGCCAGACTG GCTTGTCTGT AATCAATCTA GGCTTCG.GC CTGGATGCAC TTGCAGGCTA ..TGCCTGCC
{Rhizo3}   AGCCAGACTG GCTTGTCTGT AATCAGTCTA AGCTTCG.GC TTGGATGCAC TTGCAGGCTA ..TGCCTGCC
{Rhizo1}   AGCCAGACTG GCTTGTCTGT AATCAATCTA GGTTTCGTGC CTGGATGCAC TTGCAGACTA TTTGCCTGCC
{Mucor_}   AGCCAGACTG GTTTGACTGT AATCAACCTA GAATTCGTTC .TGGGTGCAC TTGCAGTCTA ..TACCTGCC
{C_Terr}   AGTCAGTCAT GTCTATTGGA CTCAGCCGGT TCT......G CCGGTGTACT TCCTTTAGAT GGGGTCAAC.
{F_Caps}   AGTCAGTCAT GTCTATTGGA CTCAGCCGGT TCT......G CCGGTGTATT TCCTTTAGAT GGGGTCAAC.
{F_Unig}   AGTCAGTCGT GCTCAATGGA CTCAGCCG.. TTC......T GCGGTGTATT TCCATTGGGT GGGGTCAAC.
{C_Neob}   AGTCAGTCGT GTCTATTGGG TTCAGCCAGC TCT......G CTGGTGTATT CCCTTTAGA. CGGGTCAAC.
{F_Neoc}   AGTCAGTCGT GTCTATTGGG TTCAGCCAGC TCT......G CTGGTGTATT CCCTTTAGA. CGGGTCAAC.
{F_Neod}   AGTCAGTCGT GTCTATTGGG TTCAGCCAGT TCT......G CTGGTGTATT CCCTTTAGA. CGGGTCAAC.
{C_Neof}   AGTCAGTCGT GTCTATTGGG TTCAGCCAGT TCT......G CTGGTGTATT CCCTTTAGA. CGGGTCAAC.
{T_Beig}   AGTCAGTCGT GTTCTTTGGA TTCAGCCAGT TCT......G CTGGTCTACT TCCTTGGAA. CGGGTCAAC.
{C_Laur}   AGTCAGTCGT GTCTGGGAGG CTCAGCCGGT TCT......G CCGGTGTATT CCTCTCAGA. CGGGTCAAC.
{Beauve}   GACCAGACTT GGGCTTGGTT GATCATCCGG GGTTC.TCC. CCGGTGCACT CTTCC.GGCC CAGGCCAGC.
{Fusari}   GACCAGACTT GGGCTTGGTT AATCATCTGG GGTTC.TCY. CCAGTGCACT TTTCC.AGTC CAGGCCAGC.
{Acremo}   GACCAGACTT GGGCTCGGTG AATCATCCGG CGTTC.TCG. CCGGTGCACT TTGCC.GTCC CAGGCCAGC.
{Paecil}   GACCAGACTT GGGCCCGGTG GATCATCCAG CGTTC.TCG. CTGGTGCACT CCGCCGGGTT CAGGCCAGC.
{P_Boyd}   GACCAGACTT GTGCCCGTCG AATCAGCCGC CGCTCGTCG. GCGGCGCACT TCGGCGGGCT CAGGCCAGC.
{S_Brum}   GACCAGACTC GCGCCCGTCG GATCAGCCGT CGCTCGTCG. GCGGCGCACT CCGGCGGGCT CGGGCCAGC.
{S_Brev}   GACCAGACTT GCGCCCGTCG GATCAACCGT CGCTTG.CG. GCGGCGCACT CCGGCGGGCT CAGGCCAGC.
{Sporot}   GACCAGACTT GCGCCYCGCG GACCACCCGG CGTTC.TCG. CCGGTGCACT CTGCGKKGCG CAGGCCAGC.
{B_Derm}   GACCAGAGTC GGCCGTGGGG GTTCAGCGGG CATTCGT.TG CCCGTGACT CCCCCACGGG CGGGCCAGC.
{H_Caps}   GAYCAGAGTC GGCCGYGGGG GTTCAGCGGG CATTCGT.TG CCCGTGCAAT CCCCCGCGGC CGGGCCAGC.
{A_Nidu}   GACCAGACTC GGCCCC.GGG GTTCARCCAG CACTCG..TG CTGGTGTACT TCCCCGGGGG CGGGCCAGC.
{A_Ungu}   GACCAGACTC GGCCTC.GGG GTTCAGCCAG CACTCG..TG CTGGTGTACT TCCCCGGGGG CGGGCCAGC.
{A_Ustu}   GACCAGACTC GGCCCC.GGG GTTCAGCCAG CACTCG..TG CTGGTGTACT TCCCCGGGGG CGGGCCAGC.
{A_Clav}   GACCAGACTC GCTCGC.GGG GTTCAGCCGG CATTCG..TG CCGGTGTACT TCCCCGTGGG CGGGCCAGC.
{A_Fumi}   GACCAGACTC GCCCGC.GGG GTTCAGCCGG CATTCG..TG CCGGTGTACT TCCCCGTGGG CGGGCCAGC.
{A_Flav}   GACCAGACTC GCCTCC.AGG GTTCAGCCGG CATTCG..TG CCGGTGTACT TCCCTGGGGG CGGGCCAGC.
{A_Ochr}   GACCAGACTC GCCCGC.GGG GTTCAGCCGG CATTCG..TG CCGGTGTACT TCCCCGCGGG CGGGCCAGC.
{A_Nige}   GACCAGACTC GCCCGC.GGG GTTCAGCCGG CATTCG..TG CCGGTGTACT TCCCCGTGGG CGGGCCAGC.
{A_Terr}   AACCAGACTC GCTCGC.GGG GTTCAGCCGG GCTTCG..GC CCGGTGTACT TCCCCGCGGG CGGGCCAGC.
{A_Glau}   GACCAGACTC GCTTCC.GGG GTTCAGCCGG CTTTCG..GG CCGGTGTACT TCCCCGGGGG CGGGCCAGC.
{Penici}   GACCAGACTC GCCCAC.GGG GTTCAGCCGG CATTCG..TG CCGGTGTACT TCCCCGCGGG CGGGCCAGC.
{C_Immi}   AACCAGACTC GGTCGTGGGG GCTCAGCGGG CATGAGT.GC CCGTGTACTC CCCCATGCTC CGGGCCAGC.
{Bipola}   AGCCAGACTT GCTTGCAGTT GCTCATCCGG GCTTT.T.GC CCGGTGCACT CTTCTGCAGG CAGGCCAGC.
{Curvul}   AGCCAGACTT GCTTGCAGTT GCTCATCCGG GCTTT.T.GC CCGGTGCACT CTTCTGCAGG CAGGCCAGC.
{Chryso}   AACCAGACTT GCGCGCGGCC GATCATCCGG TGTTC.T.CA CCGGTGCACT CGGCCGTGCT CAGGCCAGC.
{Clados}   AACCAGACTT GCTCGCGGT. GTTCCGCCGG TCTTC.T.GA CCGGTCTACT CGCCGCGTTG CAGGCCAGC.
```

Figure 2

```
{Malbra}  AGACAGACTC GAGCGCGGGG GCTCAGCGGG TATTGTTATG CCCGTGCACT CCCCCGCGCC CGGGCCAGC.

{C_Para}  GATCAGACTT GGTATTTTGT ATG..TTACT CTCTCGGGG. ..GTGGCCTC TACAGTTTAC CGGGCCAGC.

{C_Trop}  GATCAGACTT GGTATTTTGT ATG..TTACT TCTTCGGGG. ..GTGGCCTC TACAGTTTAT CGGGCCAGC.

{C_Albi}  GATCAGACTT GGTATTTTGC ATG..CTGCT CTCTCGGGG. ..GCGGCCGC TGCGGTTTAC CGGGCCAGC.

{C_Guil}  GATCAGACTC GATATTTTGT GAGCCTTGCC TTCGTGGCG. ..GGGTGACC CGCAGCTTAT CGGGCCAGC.

{C_Glab}  GATCAGACAT GGTGTTTTGC GCCCCTTGCC TCTCGTGGGC TTGGGACTCT CGCAGCTCAC TGGGCCAGC.

{S_Cere}  GATCAGACAT GGTGTTTTGT GCCCTCTGCT CCTTGTGGGT AGGGGAATCT CGCATTTCAC TGGGCCAGC.

{C_Kefy}  GATCAGACAT GGCGTTTGCT .......... .......... .........T CGGCTTTCGC TGGGCCAGC.

{Geotri}  AATCAGACTT GGTGCTGT.. .TGTTCAACT RTGTTTCGGC ATAGTGTACT CAGCAGTACT AGGCCAAGG.

{C_Lusi}  AAGCAGACAC GGT....... .......... .......... .......... .....TTTAC CGGGCCAGC.

{C_Krus}  CGCCCGACAT GGGGATTGCG CACCGCTGCC TCTCGTGGGC ..GGCGCTCT GGGCTTTCCC TGGGCCAGC.

{Blasch}  .......... .......... .......... .......... .......... .......... ..........

71                                                                                    140
{Rhizo2}  AACGACAATT TGACTTGAGG GAAAAAACTA GGGGAAATGT GGCC...... CACTTGTGGG TGTTATAGTC {Rhizo3}  AACGACAATT TGGCTTGAGG GAAAAAACTA AGGGAAATGT GGCC...... CATCCGTGGG TGTTATAGTC {Rhizo1}  AACGACAATT TTTTTTGAGT GTAAAAACTA TTGGAAATGT GGCCAATATT TATTTATTGG TGTTATAGTC {Mucor_}  AACAACAGTT TGATTTGGAG GAAAAAATTA GTAGGAATGT AGCC...... ....TCTCGA GGTGTTATAG {C_Terr}  .ATCAGTTTT .GATCGCTGG AAAAGGGCAG GAGGAATGTA GCACTC.TCG GGTGAACTTA TAGCCTTCTG {F_Caps}  .ATCAGTTTT .GACCGTTGG ATAAAGGCAG GAAGAATGTA GCACTC.TCG GGTGAACTTA TAGCTTCTTG {F_Unig}  .ATCAGTTTT .GATCGCTGG ATAAAGGCAG GAGGAATGTA GCACCC.CCG GGTGAACTTA TAGCCTCTTG {C_Neob}  .ATCAGTTCT .GATCGGTGG ATAAGGGCTG GAGGAATGTG GCACTCTTCG GGGTGTGTTA TAGCCTCCTG {F_Neoc}  .ATCAGTTCT .GATCGGTGG ATAAGGGCTG GAGGAATGTG GCACTCTTCG GGGTGTGTTA TAGCCTCCTG {F_Neod}  .ATCAGTTCT .GATCGGTGG ATAAGGGCTG GAGGAATGTG GCACTCTTCG GGGTGTGTTA TAGCCTCCTG {C_Neof}  .ATCAGTTCT .GATCGGTGG ATAAGGGCTG GGGGAATGTA GCACTCTTCG GAGTGTGTTA TAGCCTCCTG {T_Beig}  .ATCAGTTTT .GTCCGGTGG ATAAAGGTAG TAGGAATGTG ..ACTTCTCC GGAAGTGTTA TAGCCTATTA {C_Laur}  .ATCAGTTTT .GTCCGACGG ATAATGGCGG CGGGAAAGTA GCAC..CTCC GGGTGTGTTA TAGCCCGCTG {Beauve}  .ATCAGTTCG CCCT.GGGGG ACAAAGGCTT CGGGAACGTG GCTCTCTCC. .....GGGGA ..........

{Fusari}  .ATCAGTTTT CSCC.GGGGG ATAAAGRCTT CGGGAATGTG GCTCYCYYC. .....GGGGA ..........

{Acremo}  .ATCAGTTCG CGCC.GGGGG ATAAAGGTTT CGGGAATGTA GCTCCTTC.. ......GGGA ..........

{Paecil}  .ATCAGTTCG CCGC.GGGGG AAAAAGGCTT CGGGAACGTG GCTCCTAC.. ......GGGA ..........

{P_Boyd}  .ATCAGTTCG CTGCAGGGGG AGAAAGGCGA TGGGAATGTG GCTC..TTC. .......GGA ..........

{S_Brum}  .ATCAGTTCG CCTCGGGGGG AGAAAGGCGG CGGGAATGTG GCTC..TAC. .......GGA ..........

{S_Brev}  .ATCAGTTCG .TCCGGGGGG AGAAAGGCGG CGGGAATGTG GCTC..TTC. .......GGA ..........

{Sporot}  .ATCGGTTCT C.CCAGGGGG ACAAAGGCCG CGGGAACGTA GCTCCTTCG .........GGA ..........

{B_Derm}  .GTCGGTTTC .GACGGCCGG TCAAAGGCCC CCGGAATGTG TCGCCTCTC. ....GGGG.C ..........

{H_Caps}  .GTCGGTTTC .GACGCCGG TCAAAGGCCC CCGGAATGTG TCGCCTCTC. ....GGGG.C ..........

{A_Nidu}  .GTCGGTTTG .GGCGGCCGG TCAAAGGCCC CAGGAATGTA TCGCCCTCC. ....GGGGTT ..........

{A_Ungu}  .GTCGGTTTG .GGCGGCCGG TCAAAGGCCC CAGGAATGTA TCACCCTCC. ....GGGGTT ..........

{A_Ustu}  .GTCGGTTTG .GGCGGCCGG TCAAAGGCCC CAGGAATGTG TCGCCCTCC. ....GGGG.C ..........
```

-continued

Figure 2

```
{A_Clav}  .GTCGGTTTG .GGCGGCCGG TCAAAGGCCT CCGGAATGTA TCACCTCTC. ....GGGG.T ..........
{A_Fumi}  .GTCGGTTTG .GGCGGCCGG TCAAAGGCCC TCGGAATGTA TCACCTCTC. ....GGGG.T ..........
{A_Flav}  .GTCGGTTTG .GGCGGCCGG TCAAAGGCTC CCGGAATGTA GTGCCCTYC. ....GGGG.C ..........
{A_Ochr}  .GTCGGTTTG .GGCGGCCGG TCAAAGGCCC CCGGAATGTA GCACCCTTC. ....GGGG.T ..........
{A_Nige}  .GTCGGTTTG .GGCGGCCGG TCAAAGGCCC CTGGAATGTA GTRCCCTCC. ....GGGG.Y ..........
{A_Terr}  .GTCGGTTTG .GGCGGCCGG TCAAAGGCCT CCGGAATGTA GCGCCCTTC. ....GGGG.C ..........
{A_Glau}  .GTCGGTTTG .GGCGGCCGG TCAAAGGCCC CTGGAATGTA ACGCCTCTC. ....GGGG.C ..........
{Penici}  .GTCGGTTTG .GKCGGCCGG TCAAAGGCCC TCGGAATRTA ACGCCCCCC. ....GGGG.C ..........
{C_Immi}  .ATCAGTTCT .GGCGGTTGG TTAAAGGCCT CTGGAATGTA TCGTCCTCC. .....GGGAC ..........
{Bipola}  .ATCAGTTTG .GGCGGTGGG ATAAAGGTCT CTGTCACGTA CCTTCCTTC. ....GGGTTG ..........
{Curvul}  .ATCAGTTTG .GGCGGTGGG ATAAAGGTCT CTGACACGTT CCTTCCTTC. ....GGGTTG ..........
{Chryso}  .ATCGGTTTT .GGCGGCTGG ATAAAGGCCC TAGGAATGTG GCTCCTCTC. ....GGGGAG ..........
{Clados}  .ATCGTCTGG .TGCCGCTGG AT.AAGACTT GAGGAATGTA GCTCCCTCG. ....GGAGTG ..........
{Malbra}  .ATCAGTTTT .GGCGGCCGG TCAAAGGCCC TTGGAATGTA TCGTCCTCC. ....GGG.AC ..........
{C_Para}  .ATCAGTTT. .GAGCGGTAG GATAAGTGCA AAGAAATGTG GCACTGCTTC ....GGTAGT ..........
{C_Trop}  .ATCAGTTT. .GGGCGGTAG GAGAATTGCG TTGGAATGTG GCACGGCTTC ....GGTTGT ..........
{C_Albi}  .ATCGGTTTG .GAGCGGCAG GATAATGGCG GAGGAATGTG GCACGGCTTC ....TGCTGT ..........
{C_Guil}  .ATCGGTTT. .GGGCGGTAG GATAATGGCG TAGGAATGTG ACTTTRCTTC ....GGTGAA ..........
{C_Glab}  .ATCGGTTTT .G.GCGGCCG GAAAAAACCT AGGGAATGTG GCTCTGCGCC TCGGTGTAGA ..........
{S_Cere}  .ATCAGTTTT .G.GTGGCAG GATAAATCCA TAGGAATGTA GCTTGCCTC. .....GGTAA ..........
{C_Kefy}  .ATCAGTTTT .A.GCGGTTG GATAAATCCT CGGGAATGTG GCTCTGCTTC ....GGTAGA ..........
{Geotri}  .TGGGGTGTT .TGGGAGT.. GAAAAAGAAG TAGGAACGTA ACTCTTC... .......GGA ..........
{C_Lusi}  .GTC.GAAAA .GGGGGGAGG AACAAGAACT CGAGAATGTG GCGCGCACCT TCGGGYGCGC ..........
{C_Krus}  .ATCGGTTCT .TGCTGCAGG AGAAGGGGTT CTGGAACGTG GCTCTTC... .......GGA ..........
{Blasch}  .......... .......... .......... .......... .......... .......... ..........

141                                                                         210
{Rhizo2}  CCTTAGAAAA TACCTTGGGT TGGATTGAGG AACGCAGCGA ATG....... .......... ...CTTATTG
{Rhizo3}  CCTTAGAAAA TACCTTGGGC TGGATTGAGG TACGCAGCGA ATG....... .......... ...CTATTTG
{Rhizo1}  CTTTAGAAAA TACCTTGAAT TGGATTGAGG AACGCAGCGA ATGCTTCTCT TTnGAGGCAA AGTCTTTTAT
{Mucor_}  CCTACTATCA TACTCTGGAT TGGACTGAGG AACGCAGCGA ATGCCWTTAG GCRAGATTGC TGGGTGCTTT
{C_Terr}  TCGTATACAG TGGTTGGGAC TGAGGAACGC AGCATGCCTT TATGGCCGGG GTTCGCCCAC GTACATGCTT
{F_Caps}  TCACATACAA TGGTTGGGAC TGAGGAACGC AGCATGCCTT TATGGCCGGG ATTCGTCCAC GTACATGCTT
{F_Uniq}  TCACATACAG TGGTTGGGAC TGAGGAACGC AGCATGCCTT TATGGCCGGG ATTCGTCCAC GTACATGCTT
{C_Neob}  TCGCATACAC TGGTTGGGAC TGAGGAATGC AGCTCGCCTT TATGGCCGGG GTTCGCCCAC GTTCGAGCTT
{F_Neoc}  TCGCATACAC TGGTTGGGAC TGAGGAATGC AGCTCGCCTT TATGGCCGGG GTTCGCCCAC GTTCGAGCTT
{F_Neod}  TCGCATACAC TGGTTGGGAC TGAGGAATGC AGCTCGCCTT TATGGCCGGG GTTCGCCCAC GTTCGAGCTT
{C_Neof}  TCGCATACAC TGGTTGGGAC TGAGGAATGC AGCTCGCCTT TATGGCCGGG GTTCGCCCAC GTTCGAGCTT
{T_Beig}  TCACATACAC TGGGTGAGAC TGAGGACTGC AGCTCGCCTT TATGGCCGGC CTTCGGGCAC GTTCGAGCTT
{C_Laur}  TCGCATACGC CGGATGAGAC TGAGGCATGC AGCTCGCCTT TATGGCAGGG GTTCGCCCAC TTTCGAGCTT
{Beauve}  .........G TGTTATAGCC CGTTGCGTAA TACC.CTGTG GCGGACTGAG GTTCGCG... ..CATTCGCA
```

-continued

Figure 2

```
{Fusari}    ........G TGTTATAGCC CGTTGYGTAA TACC.CTGGB GGGGACTGAG GTTCGCG... ..CWTCTGCA {Acremo}    ........G TGTTATAGCC CGTTGCGTAA TACC.CTGGC GTGGACTGAG GTCCGCG... ..C.TCTGCA {Paecil}    ........G TGTTATAGCC CGTTGCATAA TACC.CTGGG GCGGACTGAG GTTCGCG... ..C.TCCGCA {P_Boyd}    ........G TGTTATAGCC CGCCGCGCAA TACC.CCTCG GCGGACTGAG GACCGCG... ..CATCTGCA {S_Brum}    ........G TGTTATAGCC CGCCGCGTAA TACC.CCCGG GCGGACTGAG GACCGCG... ..CGTATGCA {S_Brev}    ........G TGTTATAGCC CGCCGTGTAA TACC.CTCGG GTGGACTGAG GACCGCG... ..CGTATGCA {Sporot}    ........G TGTTATAGCC CGCGGCGGCA TGCC.CCTGG GGGGACCGAG GACCGCG... ..CTTCGGCA {B_Derm}    ........G TCTTATAGCC GGGGGTGCAA TGCGGCCAGT CGGGACCGAG GAACGCG... ..CTTCGGCA {H_Caps}    ........G TCTTATAGCC GGGGGTGCAA TGCGGCCAGT CGGGACCGAG GAACGCG... ..CTCCGGCA {A_Nidu}    ........G TCTTATAGCC TGGGGTGCAA TGCGGCCAGC CCGGACCGAG GAACGCG... ..CTTCGGCA {A_Ungu}    ........G TCTTATAGCC TGGGGTGCAA TGCGGCCAGC CTGGACCGAG GAACGCG... ..CTTCGGCA {A_Ustu}    ........G TCTTATAGCC TGGGGTGCAA TGCGGCCAGC CCGGACCGAG GAACGCG... ..CTTCGGCA {A_Clav}    ........G TCTTATAGCC GGGGGTGCAA TGCGGCCTGC CTGGACCGAG GAACGCG... ..CTTCGGCT {A_Fumi}    ........G TCTTATAGCC GAGGGTGCAA TGCGGCCTGC CTGGACCGAG GAACGCG... ..CTTCGGCT {A_Flav}    ........A CCTTATAGCC GGGAGTGCAA TGCGGCCAGC CTGGACCGAG GAACGCG... ..CTTCGGCA {A_Ochr}    ........G CCTTATAGCC GGGGGTGCAA TGCGGCCAGC CTGGACCGAG GAACGCG... ..CTTCGGCA {A_Nige}    ........A CCTTATAGCC AGGGGTGCAA TGCGGCCAGC CTGGACCGAG GAACGCG... ..CTTCGGCA {A_Terr}    ........G CCTTATAGCC GGGGGTGCAA TGCGGCCAGC CTGGACCGAG GAACGCG... ..CTTCGGCA {A_Glau}    ........G CCTTATAGCC AGGGGTGTCA TGCGGCCAGC CTGGACCGAG GAACGCG... ..CTTCGGCA {Penici}    ........G TCTTATAGCC GAGGGTGCCA TGCGGCCAGC MCAGACCGAG GAACGCG... ..CTTCGGCT {C_Immi}    ........G TCTTATAGCC AGGGGCGCAA TGCGGCCAGC CGGGACTGAG GAACGCG... ..CTTCGGCA {Bipola}    ........G CCATATAG.G GGAGACGTCA TACCACCAGC CTGGACTGAG GTCCGCG... ..CATCTGCT {Curvul}    ........G CCATATAG.G GGAGACGTCA TACCACCAGC CTGGACTGAG GTCCGCG... ..CATCTGCT {Chryso}    ........T GTTATAGC.C TAGGGTGCAA TGCAGCCTGC TGGGACCGAG GACCGCG... ..CTTCGGCT {Clados}    .......... ...TTATA.G CCTCTTGTGA TGCAGCGAGC GCCGGGCGAG GTCCGCG... ..CTTCGGCT {Malbra}    ........G TCTTATAGCC AAGGGTGCAA TGCGGCCAGC CGGGACTGAG GAACGCG... ..CTTCGGCA {C_Para}    ........G TGTTATAGTC T.TTGTC.GA TACTGCCAGC TTAGACTGAG GACTGCG..G CTTCG.GCCT {C_Trop}    ........G TGTTATAGCC T.TCGTC.GA TACTGCCAGC CTAGACTGAG GACTGCG..G TTTAT.ACCT {C_Albi}    ........G TGTTATAGCC T.CTGAC.GA TGCTGCCAGC CTAGACCGAG GACTGCG..G TTTTTAACCT {C_Guil}    ........G TGTTATAGCC T.GCGTT.GA TGCTGCCTGC CTAGACCGAG GACTGCG..A TTTT..ATCA {C_Glab}    ........G TGTTATAGCC C.TGGGG.AA TACGGCCAGC CGGGACCGAG GACTGCGATA CTTGTTATCT {S_Cere}    ........G TATTATAGCC T.GTGGG.AA TACTGCCAGC TGGGACTGAG GACTGCGACG TAAG...TCA {C_Kefy}    ........G TGTTATAGCC C.GTGGG.AA TACAGCCAGC TGGGACTGAG GATTGCGACT TTTG...TCA {Geotri}    ........G TGTTATAGCC T.ACTTT.CA TAGCTCCTCA GGCGCCTCAG GACTGCG... ..CTTCGGCA {C_Lusi}    ........G TGTTATAGCT C.GTGTT.GA CGCCTCCATC CCTTTTCGAG GCCTGCGAT. .......TCT {C_Krus}    ........G TGTTATAGCC A.GGGCCAGA TGCTGCGTGC GGGGACCGAG GACTGCGGCC GTGTAGGTCA {Blasch}    .....TGAAA TTGTTGAAAG GGAAGGCGAT GGTAGGAATA AGAGGCTGCG GTTTGAAATA ATTGTTTTTC 211                                    250
{Rhizo2}    GCGAGTTTTC CAGGAAGGT. .....TTTCT GAGGTACTAC
```

-continued

Figure 2

| | | | |
|---|---|---|---|
| {Rhizo3} | GCGAGTTGGC | TGGGAATAT. | .....TTTCT GAGGTGCTTT |
| {Rhizo1} | TGGGATTTAC | GGATCAGAC. | .....TGTGG CATTGTCACA |
| {Mucor_} | CGCTAATAAA | TGTTAGAATT | TCTGCTTCGG GTGGTGCTAA |
| {C_Terr} | AGG..ATGTT | GACATAATGG | CTTTAAACGA CCCGTCTTGA |
| {F_Caps} | AGG..ATGTT | GACATAATGG | CTTTAAACGA CCCGTCTTGA |
| {F_Uniq} | AGG..ATGTT | GACATAATGG | CTTTAAACGA CCCGTCTTGA |
| {C_Neob} | AGG..ATGTT | GACAAAATGG | CTTTAAACGA CCCGTCTTGA |
| {F_Neoc} | AGG..ATGTT | GACAAAATGG | CTTTAAACGA CCCGTCTTGA |
| {F_Neod} | AGG..ATGTT | GACAAAATGG | CTTTAAACGA CCCGTCTTGA |
| {C_Neof} | AGG..ATGTT | GACAAAATGG | CTTTAAACGA CCCGTCTTGA |
| {T_Beig} | AGG..ATGTT | GACATAATGG | CTTTAAACGA CCCGTCTTGA |
| {C_Laur} | AGG..ATGTT | GACGTAATGG | CTTTAAACGA CCCGTCTTGA |
| {Beauve} | AGG..ATGCT | GGCGTAATGG | TCATCAGTGA CCCGTCT... |
| {Fusari} | AGG..ATGCT | GGCGTAATGG | TCATCAACGA CCCGTCTTGA |
| {Acremo} | AGG..ATGCT | GGCGTAATGG | TCATCAGTGA CCCGTCTTGA |
| {Paecil} | AGG..ATGCT | GGCGTAATGG | TCATCAGCGA CCCGTCTTGA |
| {P_Boyd} | AGG..ATGCT | GGCGTAATGG | TCGTCAGCGA CCCGTCTTGA |
| {S_Brum} | AGG..ATGCT | GGCGTAATGG | TCGTCAGCGA CCCGTCTTGA |
| {S_Brev} | AGG..ATGCT | GGCGTAATGG | TCGTCAGCGA CCCGTCTTGA |
| {Sporot} | AGG..ATGCT | GGCGTAATGG | TCACCAGCGA ACCGTCTTGA |
| {B_Derm} | CGG..ACGCT | GGCTTAATGG | TCGTAAGCGA CCCGTCTTGA |
| {H_Caps} | CGG..ACGCT | GGCTTAATGG | TCGTCAGCGA CCCGTCTTGA |
| {A_Nidu} | CGG..ACGCT | GGCGTAATGG | TCGCAAACGA CCCGTCTTGA |
| {A_Ungu} | CGG..ACGCT | GGCATAATGG | TTGCAAACGA CCCGTCTTGA |
| {A_Ustu} | CGG..ACGCT | GGCGTAATGG | TCGCAAACGA CCCGTCTTGA |
| {A_Clav} | CGG..ACGCT | GGCGTAATGG | TCGTAAATGA CCCGTCTTGA |
| {A_Fumi} | CGG..ACGCT | GGCGTAATGG | TCGTAAATGA CCCGTCTTGA |
| {A_Flav} | CGG..ACGCT | GGCATAATGG | TCGYAAACGA CCCGTCTTGA |
| {A_Ochr} | CGG..ACGCT | GGCATAATGG | TCGTAAACGA CCCGTCTTGA |
| {A_Nige} | CGG..ACGCT | GGCATAATGG | TCGTAAACGA CCCGTCTTGA |
| {A_Terr} | CGG..ACGCT | GGCATAATGG | TTGTAAACGA CCCGTCTTGA |
| {A_Glau} | CGG..ACGCT | GGCATAATGG | TCGTAAACGA CCCGTCTTGA |
| {Penici} | CGG..ACGCT | GGCATAATGG | TCGTAAA... .......... |
| {C_Immi} | CGG..ATGCT | GGCATAATGG | TTGTAAGCGG CCCGTCTTGA |
| {Bipola} | AGG..ATGCT | GGCGTAATGG | CTGTAAGCGG CCCGTCTTGA |
| {Curvul} | AGG..ATGCT | GGCGTAATGG | CTGTAAGCGG CCCGTCTTGA |
| {Chryso} | AGG..ATGCT | GGCGTAATGG | TTGTAAGCGG CCCGTCTTGA |
| {Clados} | AGG..ATGCT | GGCGTAATGG | TCGTAATCCG CCCGTCTTGA |
| {Malbra} | CGG..ATGCT | GGCGTAATGG | CTGTAAGCGG CCCGTCTTGA |

Figure 2 (-continued)

```
{C_Para}   AGG..ATGTT GGCATAATGA TCTTAAGTCG CCCGTCTTGA

{C_Trop}   AGG..ATGTT GGCATAATGA TCTTAAGTCG CCCGTCTTGA

{C_Albi}   AGG..ATGTT GGCATAATGA TCTTAAGTCG CCCGTCTTGA

{C_Guil}   AGG..ATGCT GGCATAATGA TCCCAAACCG CCCGTCTTGA

{C_Glab}   AGG..ATGCT GGCATAATGG TTATATGCCG CCCGTCTTGA

{S_Cere}   AGG..ATGCT GGCATAATGG TTATATGCCG CCCGTCTTGA

{C_Kefy}   AGG..ATGCT GGCGTAATGG TTAAATGCCG CCCGTCTTGA

{Geotri}   AGG..ACCTT GGCATAATGA TTCTATACCG CCCGTCTTGA

{C_Lusi}   AGG..ACGCT GGCGTAATGG TTGCAAGCCG CCCGTCTTGA

{C_Krus}   CGG..ATGCT GGCAGAACGG CGCAACACCG CCCGTCTTGA

{Blasch}   GGGCCACGGT CTCCTGAGCC TGCTTTCGCA CCCGTCTTGA
```

Legend to FIG. 2:

The multiple sequence alignment shows the sequence of 28S ribosomal RNA genes amplified with primers SEQ ID NO: 1 and SEQ ID NO: 2. 21 species specific probes (SEQ ID NO: 3 to SEQ ID NO: 23) are shown underlined. Minor sequence variation among two isolate of the same organism are represented by the appropriate code (see key below). Major differences among Rhizopus species are depicted by including 3 separate Rhizopus sequences in the alignment. (The organisms in this figure are listed according to their sequence relatedness.)

Key to symbols:

(.) gap in sequence to facilitate alignment (R) A or G (W) A or T (Y) T or C (M) A or C (K) T or G (S) G or C (B) T,G or C

| | |
|---|---|
| Acremo | Acremonium species |
| A_clav | Aspergillus clavatus |
| A_flav | Aspergillus flavus |
| A_fumi | Aspergillus fumigatus |
| A_glau | Aspergillus glaucus |
| A_nidu | Aspergillus nidulans |
| A_nige | Aspergillus niger |
| A_ochr | Aspergillus ochraceus |
| A_terr | Aspergillus terreus |
| A_ungu | Aspergillus unguis |
| A_ustu | Aspergillus usfus |
| Beauve | Beauveria species |
| Bipola | Bipolaris species |
| Blasch | Blastoschizomyces species |
| B_derm | Blastomyces dermatitidis |
| Chryso | Chrysosporium species |
| Clados | Cladosporium species |
| Curvul | Curvularia species |
| C_albi | Candida albicans |
| C_glab | Candida glabrata |
| C_guil | Candida guilliermondii |
| C_immi | Coccidioides immitis |
| C_kefy | Candida kefyr |
| C_krus | Candida krusei |
| C_laur | Cryptoococcus laurentii |
| C_lusi | Candida lusitaniae |
| C_neob | Cryptococcus neoformans var gattii serotype B |
| C_neof | Cryptococcus neoformans serotype A |
| C_para | Candida parapsilosis |
| C_terr | Cryptococcus terreus |
| C_trop | Candida tropicalis |
| Fusari | Fusarium species |
| F_caps | Filobasidium capsuligenum |
| F_neoc | Filobasidiella (Cryptococcus) neoformans var bacillispora serotype C |
| F_neod | Filobasidiella (Cryptococcus) neoformans var neoformans serotype D |
| F_unig | Filobasidium uniguttulatum |
| Geotri | Geotrichum species |
| H_caps | Histoplasma capsulatum |
| Malbra | Malbranchea species |
| Mucor_ | Mucor species |
| Paecil | Paecilomyces species |
| Penici | Penicillium species |
| P_boyd | Pseudallescheria boydii |
| Rhizo1 | Rhizopus species isolate #1 |
| Rhizo2 | Rhizopus species isolate #2 |
| Rhizo3 | Rhizopus species isolate #3 |
| Sporot | Sporothrix schenkii |
| S_brev | Scopulariopsis brevicaulis |
| S_brum | Scopulariopsis brumpti |
| S_cere | Saccharomyces cerevisiae |
| T_beig | Thichosporon beigelii |

Further variations of the invention that utilize any of the named sequences will be apparent to those with ordinary skill in the art. The following examples illustrate various aspects of the invention but are not intended to limit its usefulness.

EXAMPLE 1

Testing Probes SEQ ID NO: 3 to SEQ ID NO: 23 for Hybridization Specificilty.

Probes listed in SEQ ID NO: 3 to SEQ ID NO: 23 were tested for specificity against their target organisms. Probe SEQ ID NO: 5 for *Candida albicans* was the first one tested against a panel of fungi taken from the Mayo Clinic collection. 28S rDNA from Acremonium sp., *Aspergillus clavatus, Aspergillus flavus, Aspergillus fumigatus, Aspergillus glaucus, Aspergillus nidulans, Aspergillus niger, Aspergillus ochraceus, Aspergillus terreus, Aspergillus unguis, Aspergil-*

*lus ustus*, Aspergillus sp., Beauvaria sp., Bipolaris sp., *Blastomyces dermatitidis, Candida albicans, Candida glabrala, Candida guilliermondii, Candida kefyr, Candida krusei, Candida lusitaniae, Candida parapsilosis, Candida tropicalis*, Chrysosporium sp., Cladosporium sp., *Coccidioides immitis*, Cryptococcus neoformans serotype A, Curvularia sp., Fusarium sp., Geotrichum sp., *Histoplama capsulatum*, Mucor sp., Penicillium sp., *Pseudallescheria boydii*, Rhizopus sp., *Saccharomyces cerevisiae, Scopulariopsis brevicaulis, Sporothrix schenkii* and *Trichosporon beigelii* was amplified in a polymerase chain reaction using oligonucleotide probes SEQ ID NO: 1 and SEQ ID NO: 2. All PCR amplifications were carried out as hot-start reactions in a 50 ul reaction volume using Perkin-Elmer (Norwalk, Conn.) 0.5 ml thin-wall polypropylene tubes and a Perkin-Elmer thermal cycler. Reagents added to the tube initially were 2.5 ul of 10× PCR buffer (100 mM tris pH 8.3, 500 mM KCl, 15 mM $MgCl_2$), 5.0 ul of 50% glycerol/1 mM cresol red, 8.0 ul of dNTP mix (1.25 mM each of dATP, dGTP, dTTP and dCTP), 11 picomoles of each nucleic acid primer and sterile water to make up a volume of 25 ul. A wax bead (Ampliwax Gem=100, Perkin-Elmer) was added and the tubes heated to 77° C. for 30 seconds and cooled to room temperature to form a wax barrier. 2.5 ul of 10X PCR buffer, 5.0 ul of 50% glycerol/1 mM cresol red, 0.2 ul Taq polymerase (AmpliTaq 5U/ul, Perkin-Elmer) and 15.3 ul of sterile water was added to the tube along with 2.0 ul of DNA from the fungal whole cell boiled lysate described above. 50 cycles of thermal cycling was carried out at 94° C.—30 sec, 50° C.—1 min, 72° C.—2 min. Five microliters of polymerase chain reaction mix from each sample was run on a 5% polyacrylamide gel to visually confirm the successful amplification of 28S rDNA from each fungus listed above. 40 ul of the remaining amplified 28S rDNA was denatured in 1 N NaOH, and half of this denatured rDNA was slot blotted on to a positively charged polysulphone based membrane equilibrated in 0.5 N NaOH. The membrane was air dried for 15 minutes and baked in a vacuum oven at 80° C. for 30 minutes. Amplified rDNA from each species was now bound and immobilized at a separate spot on the membrane. The free binding sites on the membrane were blocked by incubating the membrane for 3 hours at 40° C. in hybridization buffer (100 ml of hybridization buffer was made using 1 g non-fat milk powder, 6 g $NaH_2PO_4$, 7 g SDS, 200 ul 0.5M EDTA and adjusted to pH 7.2 with NaOH). The specific probe for *Candida albicans* (SEQ ID NO: 5) was end-labeled with radioactive phosphorus using $^{32}P$ ATP and T4 polynucleotide kinase. 50 picomoles of this probe was added to 70 milliliters of hybridization buffer and the membrane was probed at 40° C. overnight. The membrane was washed in hybridization buffer at 40° C. for 15 minutes followed by a wash in 2× SSC at 40° C. for 15 minutes. The membrane was then exposed on x-ray film for at least 1 hour. The oligonucleotide probe SEQ ID NO: 5 only hybridized to amplified 28S rDNA from *Candida albicans* (see Table 3) Under these hybridization conditions, probe SEQ ID NO: 5 is extremely specific for *Candida albicans*. The sequence of oligonucleotide probe SEQ ID NO: 5 differs from the sequences of other species of Candida by as few as 1 or 2 bases, but these mismatches are sufficient to prevent stable hybrids from forming with the other Candida species.

Probes SEQ ID NO: 3 to SEQ ID NO: 23 were tested for specificity, as described above for the *Candida albicans* probe SEQ ID NO: 5, against the same panel of fumgi listed in the preceding paragraph. The positively charged polysulphone based membrane probed with *Candida albicans* probe SEQ ID NO: 5 was washed in 0.5 N NaOH at 40° C. for 10 minutes to remove all bound *Candida albicans* probe. The membrane was sequentially probed with all probes listed in SEQ ID NO: 3 to SEQ ID NO: 23. For each subsequently tested probe, the membrane was blocked for at least 30 minutes, probe hybridization was carried out at 40–42° C. for at least 3 hours, and post-hybridization washes were done in 2× SSC for 20 minutes. The membrane was stripped between probings by washing in 0.5 to 1.0 N NaOH at 40–42° C. Results are listed in Tables 3 to 6.

As shown in Tables 3 to 6, each probe listed in SEQ ID NO: 3 to SEQ ID NO: 23 specifically hybridizes to only one target fungal 28S nucleic acid sequence. This specificity is essential for identifying a given species of fungus in clinical specimens containing mixed fungal organisms with a high level of reliability. The 39 organisms listed in these Tables represent a majority of organisms that are commonly isolated from clinical samples. While we have developed 21 species specific probes (SEQ ID NO: 3 to SEQ ID NO: 23) that identify a total of 19 individual organisms, the additional organisms listed in the test panel were used to ensure that our probes did not have any cross-reactivity with other fungi likely to be present in a clinical specimen. The ability to accurately and reliably diagnose, and identify to a species level, this large a number of pathogens is unmatched by any other report. The fact that we can achieve this by probing DNA amplified by a single pair of "Universal" probes (SEQ ID NO: 1 and SEQ ID NO: 2) is highly advantageous as it saves time, money and effort by providing the ability to test a single amplified target with 21 different probes (SEQ ID NO: 3 to SEQ ID NO: 23).

A GenBank search was carried out with all probes listed in SEQ ID NO: 3 to SEQ ID NO: 23 in order to determine whether similar gene sequences were present in the database. 28S sequences for *Candida albicans* and *Cryptococcus neoformans* are already present in GenBank, and as expected, the probes for *Candida albicans* and *Cryptococcus neoformans* correctly identified the 28S sequences from these two organsims. Ten other probes also matched DNA sequences from a variety of genes not related to the 28S gene (Table 7). This was expected because short stretches of sequence identity can often be found for any query sequence in unrelated genes from the same or a different organism. This observation is known to those versed in this art. In all cases, sequences that matched a probe sequence were not located within the 28S rRNA genes. Our probes are used to analyze 28S DNA that has been previously amplified in a polymerase chain reaction with our probes SEQ ID NO: 1 and SEQ ID NO: 2. Under stringent conditions, these two probes only amplify DNA from fungal 28S rRNA genes. Therefore no amplified DNA from the non-28S genes listed in Table 7 will be available for the hybridization of probes SEQ ID NO: 3 to SEQ ID NO: 23. The presence of related sequences in non-28S, unamplified genes will not be detected and will, thus, not have any effect on the sensitivity or the specificity of our detection and identification strategy.

TABLE 3

Detection of species specific 28S sequence with probes SEQ ID NO: 3 to SEQ ID NO: 8

| FUNGUS | SEQ ID: 3 | SEQ ID: 4 | SEQ ID: 5 | SEQ ID: 6 | SEQ ID: 7 | SEQ ID: 8 |
|---|---|---|---|---|---|---|
| *Acremonium sp.* | − | − | − | − | − | − |
| *Aspergillus clavatus* | − | − | − | − | − | − |
| *Aspergillus flavus* | − | − | − | − | − | − |
| *Aspergillus fumigatus* | + | − | − | − | − | − |
| *Aspergillus glaucus* | − | − | − | − | − | − |
| *Aspergillus nidulans* | − | − | − | − | − | − |
| *Aspergillus niger* | − | − | − | − | − | − |
| *Aspergillus ochraceus* | − | − | − | − | − | − |
| *Aspergillus terreus* | − | − | − | − | − | − |
| *Aspergllus unguis* | − | − | − | − | − | − |
| *Aspergillus ustus* | − | − | − | − | − | − |
| *Aspergillus sp.* | − | − | − | − | − | − |
| *Beauvaria sp.* | − | − | − | − | − | − |
| *Bipoiaris sp.* | − | − | − | − | − | − |
| *Blastomyces dermatitidis* | − | + | − | − | − | − |
| *Candida albicans* | − | − | + | − | − | − |
| *Candida glabrata* | − | − | − | − | − | − |
| *Candida guilliermondii* | − | − | − | − | − | − |
| *Candida kefyr* | − | − | − | − | − | − |
| *Candida krusei* | − | − | − | − | − | − |
| *Candida lusitaniae* | − | − | − | − | − | − |
| *Candida parapsilosis* | − | − | − | − | − | − |
| *Candida tropicalis* | − | − | − | − | − | − |
| *Chrysosporium sp.* | − | − | − | − | − | − |
| *Cladosporium sp.* | − | − | − | − | − | − |
| *Coccidiodides immitis* | − | − | − | + | − | − |
| *Cryptococcus neoformans* | − | − | − | − | + | + |
| *Curvularia sp.* | − | − | − | − | − | − |
| *Fusarium sp.* | − | − | − | − | − | − |
| *Geotrichum sp.* | − | − | − | − | − | − |
| *Histoplasma capsulatum* | − | − | − | − | − | − |
| *Mucor sp.* | − | − | − | − | − | − |
| *Penicillium sp.* | − | − | − | − | − | − |
| *Pseudillescheria boydii* | − | − | − | − | − | − |
| *Rhizopus sp.* | − | − | − | − | − | − |
| *Saccharomyces cerevisiae* | − | − | − | − | − | − |
| *Scopulariopsis brevicauiis* | − | − | − | − | − | − |
| *Sporothrix schenckii* | − | − | − | − | − | − |
| *Trichosporon beigelii* | − | − | − | − | − | − |

+ Positive
− Negative after 20 minute wash in 2X SSC

TABLE 4

Detection of species specific 28S sequence with probes SEQ ID NO: 9 to SEQ ID NO: 14

| FUNGUS | SEQ ID: 9 | SEQ ID: 10 | SEQ ID: 11 | SEQ ID: 12 | SEQ ID: 13 | SEQ ID: 14 |
|---|---|---|---|---|---|---|
| *Acremonium sp.* | − | − | − | − | − | − |
| *Aspergillus clavatus* | − | − | − | − | − | − |
| *Aspergillus flavus* | − | − | − | − | − | − |
| *Aspergillus fumigatus* | − | − | − | − | − | − |
| *Aspergillus glaucus* | − | + | − | − | − | − |
| *Aspergillus nidulans* | − | − | − | − | − | − |
| *Aspergillus niger* | − | − | + | − | − | − |
| *Aspergillus ochraceus* | − | − | − | − | − | − |
| *Aspergillus terreus* | − | − | − | + | − | − |
| *Aspergllus unguis* | − | − | − | − | − | − |
| *Aspergillus ustus* | − | − | − | − | − | − |
| *Aspergillus sp.* | − | − | − | − | − | − |
| *Beauvaria sp.* | − | − | − | − | − | − |
| *Bipoiaris sp.* | − | − | − | − | − | − |
| *Blastomyces dermatitidis* | − | − | − | − | − | − |
| *Candida albicans* | − | − | − | − | − | − |
| *Candida glabrata* | − | − | − | − | + | − |
| *Candida guilliermondii* | − | − | − | − | − | + |

TABLE 4-continued

Detection of species specific 28S sequence with probes SEQ ID NO: 9 to SEQ ID NO: 14

| FUNGUS | SEQ ID: 9 | SEQ ID: 10 | SEQ ID: 11 | SEQ ID: 12 | SEQ ID: 13 | SEQ ID: 14 |
|---|---|---|---|---|---|---|
| *Candida kefyr* | − | − | − | − | − | − |
| *Candida krusei* | − | − | − | − | − | − |
| *Candida lusitaniae* | − | − | − | − | − | − |
| *Candida parapsilosis* | − | − | − | − | − | − |
| *Candida tropicalis* | − | − | − | − | − | − |
| *Chrysosporium sp.* | − | − | − | − | − | − |
| *Cladosporium sp.* | − | − | − | − | − | − |
| *Coccidioides immitis* | − | − | − | − | − | − |
| *Cryptococcus neoformans* | − | − | − | − | − | − |
| *Curvularia sp.* | − | − | − | − | − | − |
| *Fusarium sp.* | − | − | − | − | − | − |
| *Geotrichum sp.* | − | − | − | − | − | − |
| *Histoplasma capsulatum* | + | − | − | − | − | − |
| *Mucor sp.* | − | − | − | − | − | − |
| *Penicillium sp.* | − | − | − | − | − | − |
| *Pseudillescheria boydii* | − | − | − | − | − | − |
| *Rhizopus sp.* | − | − | − | − | − | − |
| *Saccharomyces cerevisiae* | − | − | − | − | − | − |
| *Scopulariopsis brevicauiis* | − | − | − | − | − | − |
| *Sporothrix schenckii* | − | − | − | − | − | − |
| *Trichosporon beigelii* | − | − | − | − | − | − |

+ Positive
− Negative after 20 minute wash in 2X SSC

TABLE 5

Detection of species specific 28S sequence with probes SEQ ID NO: 15 to SEQ ID NO: 20

| FUNGUS | SEQ ID: 15 | SEQ ID: 16 | SEQ ID: 17 | SEQ ID: 18 | SEQ ID: 19 | SEQ ID: 20 |
|---|---|---|---|---|---|---|
| *Acremonium sp.* | − | − | − | − | − | − |
| *Aspergillus clavatus* | − | − | − | − | − | − |
| *Aspergillus flavus* | − | − | − | − | − | − |
| *Aspergillus fumigatus* | + | − | − | − | − | − |
| *Aspergillus glaucus* | − | − | − | − | − | − |
| *Aspergillus nidulans* | − | − | − | − | − | − |
| *Aspergillus niger* | − | − | − | − | − | − |
| *Aspergillus ochraceus* | − | − | − | − | − | − |
| *Aspergillus terreus* | − | − | − | − | − | − |
| *Aspergllus unguis* | − | − | − | − | − | − |
| *Aspergillus ustus* | − | − | − | − | − | − |
| *Aspergillus sp.* | − | − | − | − | − | − |
| *Beauvaria sp.* | − | − | − | − | − | − |
| *Bipoiaris sp.* | − | − | − | − | − | − |
| *Blastomyces dermatitidis* | − | − | − | − | − | − |
| *Candida albicans* | − | − | − | − | − | − |
| *Candida glabrata* | − | − | − | − | − | − |
| *Candida guilliermondii* | − | − | − | − | − | − |
| *Candida kefyr* | + | − | − | − | − | − |
| *Candida krusei* | − | + | − | − | − | − |
| *Candida lusitaniae* | − | − | + | − | − | − |
| *Candida parapsilosis* | − | − | − | + | − | − |
| *Candida tropicalis* | − | − | − | − | + | − |
| *Chrysosporium sp.* | − | − | − | − | − | − |
| *Cladosporium sp.* | − | − | − | − | − | − |
| *Coccidioides immitis* | − | − | − | − | − | − |
| *Cryptococcus neoformans* | − | − | − | − | − | − |
| *Curvularia sp.* | − | − | − | − | − | − |
| *Fusarium sp.* | − | − | − | − | − | − |
| *Geotrichum sp.* | − | − | − | − | − | − |
| *Histoplasma capsulatum* | − | − | − | − | − | − |
| *Mucor sp.* | − | − | − | − | − | − |
| *Penicillium sp.* | − | − | − | − | − | − |
| *Pseudillescheria boydii* | − | − | − | − | − | + |
| *Rhizopus sp.* | − | − | − | − | − | − |
| *Saccharomyces cerevisiae* | − | − | − | − | − | − |

TABLE 5-continued

Detection of species specific 28S sequence with probes SEQ ID NO: 15 to SEQ ID NO: 20

| FUNGUS | SEQ ID: 15 | SEQ ID: 16 | SEQ ID: 17 | SEQ ID: 18 | SEQ ID: 19 | SEQ ID: 20 |
|---|---|---|---|---|---|---|
| *Scopulariopsis brevicauiis* | – | – | – | – | – | – |
| *Sporothrix schenckii* | – | – | – | – | – | – |
| *Trichosporon beigelii* | – | – | – | – | – | – |

+ Positive
– Negative after 20 minute wash in 2X SSC

TABLE 6

Detection of species specific 28S sequence with probes SEQ ID NO: 21 to SEQ ID NO: 23

| FUNGUS | SEQ ID: 21 | SEQ ID: 22 | SEQ ID: 23 |
|---|---|---|---|
| *Acremonium sp* | – | – | – |
| *Asperglllus clavatus* | – | – | – |
| *Asperglllus flavus* | + | – | – |
| *Aspergillus fumigatus* | – | – | – |
| *Aspergillus glaucus* | – | – | – |
| *Aspergillus nidulans* | – | – | – |
| *Aspergillus niger* | – | – | – |
| *Aspergillus ochraceus* | – | – | – |
| *Aspergillus terreus* | – | – | – |
| *Aspergillus unguis* | – | – | – |
| *Aspergillus ustus* | – | – | – |
| *Aspergillus sp.* | – | – | – |
| *Beauvaria sp.* | – | – | – |
| *Bipolaris sp.* | – | – | – |
| *Blastomyces dermatitidis* | – | – | – |
| *Candida albicans* | – | – | – |
| *Candida glabrata* | – | – | – |
| *Candida guilliermondii* | – | – | – |
| *Candida kefyr* | – | – | – |
| *Candida krusei* | – | – | – |
| *Candida lusitaniae* | – | – | – |
| *Candida parapsilosis* | – | – | – |
| *Candida tropicalis* | – | – | – |
| *Chrysosporium sp.* | – | – | – |
| *Cladosporium sp.* | – | – | – |
| *Coccidioides immitis* | – | – | – |
| *Cryptococcus neoformans* | – | – | – |
| *Curvularia sp.* | – | – | – |
| *Fusarium sp.* | – | – | – |
| *Geotrichum sp.* | – | – | – |
| *Histoplasma capsuiatum* | – | – | – |
| *Mucor sp.* | – | – | – |
| *Penicillium sp.* | – | – | – |
| *Pseudallescheria boydii* | – | – | – |
| *Rhizopus sp.* | – | – | – |
| *Saccharomyces cerevisiae* | – | – | – |
| *Scopitlariopsis brevicaulis* | – | – | – |
| *Sporothrix schenckii* | – | + | + |
| *Thichosporon beigelii* | – | – | – |

+ Positive
– Negative after 20 minute wash in 2X SSC

TABLE 7

GenBank search results listing genes from other organisms having 100% identity to probes SEQ ID NO: 3 to SEQ ID NO: 23

| | PROBE SEQ ID NO: | ORGANISM MATCHED | GENE MATCHED* (see note below) | ACCESSION NUMBER |
|---|---|---|---|---|
| *Aspergillus fumigatus* | 3 | — | — | — |
| *Blastomyces dermatitidis* | 4 | *Streptomyces verticillus* | bleomycin acetyl transferase | L26955 |
| | 4 | *Giardia muris* | upstream of rRNA genes | X65063, S53320 |
| | 4 | *Aspergillus nidulans* | uric acid-xanthine permease | X71807 |
| | 4 | *Homo sapiens* | T-cell surface glycoprotein | X16996 |
| | 4 | *Homo sapiens* | MIC2 | M16279, M22557, J03841, M22556 |
| *Candida albicans* | 5 | *Candida albicans* | 28S rRNA | L28817 |
| *Coccidioides immitis* | 6 | — | — | — |
| *Cryptococcus neoformans* | 7 | *Cryptococcus neoformans* | 28S rRNA | L14067, L14068, |

TABLE 7-continued

GenBank search results listing genes from other organisms having 100% identity to probes
SEQ ID NO: 3 to SEQ ID NO: 23

| ORGANISM MATCHED | PROBE SEQ ID NO: | ORGANISM MATCHED | GENE MATCHED* (see note below) | ACCESSION NUMBER |
|---|---|---|---|---|
| *Cryptococcus neoformans* | 8 | *Cryptococcus neoformans* | 28S rRNA | L14067, L14068, L20964 |
|  | 8 | *Escherichia coli* | 0111 cld | Z17241 |
| *Histoplasma capsulatum* | 9 | — | — | — |
| *Aspergillus glaucus* | 10 | *Pseudomonas denitrificans* | cob genes | M62866 |
| *Aspergillus niger* | 11 | — | — | — |
| *Aspergillus terreus* | 12 | Human cytomegalovirus | genome | X17403 |
|  | 12 | *Homo sapiens* | GABA receptor | L08485 |
| *Candida glabrata* | 13 | *Homo sapiens* | Class 1 MHC | X03664, X03665 |
| *Candida guilliermondii* | 14 | — | — | — |
| *Candida kefyr* | 15 | — | — | — |
| *Candida krusei* | 16 | *Pseudomonas syringae* | penicillin binding protein | L28837 |
| *Candida lusitaniae* | 17 | Chicken | AK1 | D00251 |
|  | 17 | Mouse | IL10 | M84340 |
| *Candida parapsilosis* | 18 | *Polytomella agilis* | beta-2 tubulin | M33373 |
|  | 18 | Tobacco chloroplast | genome | Z00044, S54304 |
|  | 18 | *Aedes aegypti* | amylase | L03640 |
|  | 18 | *Homo sapiens* | chromosome 13q14 | L14473 |
| *Candida tropicalis* | 19 | — | — | — |
| *Pseudallescheria boydii* | 20 | *Drosophila melanogaster* | AcTr66B | X71789 |
|  |  | Cow | actin 2 | D12816 |
| *Aspergillus flavus* | 21 | — | — | — |
| *Sporothrix schenckii* | 22 | — | — | — |
| *Sporothrix schenckii* | 23 | Sulfate reducing bacteria | FMN binding protein | D21804 |
|  | 23 | Equine herpesvirus 1 | genome | M86664 |

*Note: As discussed earlier in this document, the presence of sequences similar to probes SEQ ID NO: 3 to SEQ ID NO: 23 in genes not related to 28S does not have any effect on the specificity or sensitivity of our diagnostic strategy. Our species specific probes are used to analyze 28S DNA that has been previously amplified in a polymerase chain reaction with our probes SEQ ID NO: 1 and SEQ ID NO: 2. These two probes will not amplify DNA from any gene other than 28S in column #4 (GENE MATCHED), and therefore no amplified DNA from these non-28S genes will be available for the hybridization of probes SEQ ID NO: 3 to SEQ ID NO: 23.

* Note: As discussed earlier in this document, the presence of sequences similar to probes SEQ ID NO:3 to SEQ ID NO: 23 in genes not related to 28S does not have any effect on the specificity or sensitivity of our diagnostic strategy. Our species specific probes are used to analyze 28S DNA that has been previously amplified in a polymerase chain reaction with our probes SEQ ID NO: 1 and SEQ ID NO:2. These two probes will not amplify DNA from any gene other than 28S in column #4 (GENE MATCHED), and therefore no amplified DNA from these non-28S genes will be available for the hybridization of probes SEQ ID NO: 3 to SEQ ID NO: 23.

EXAMPLE 2
Use of Method in Example 1 to Test Clinical Specimens for Specific Fungal Organisms.

Clinical samples taken from the respiratory and gastrointestinal tract of healthy individuals almost always contain some fungal flora. Most of these fungi are non-pathogenic, but may give false positives on traditional immunochemical diagnostic tests for pathogenic fungi.

We obtained 44 clinical specimens from diverse sources ranging from sputum and incision drainage tubes, to intervertebral disc and lung biopsies. Traditional smear and culture results showed that all 44 specimens contained at least 1 type of fungus. In order to test the efficacy of our probes, we extracted DNA from all 44 clinical samples and used probes SEQ ID NO: 1 & 2 in a polymerase chain reaction to amplify fungal 28S sequences present in these samples.

DNA was extracted from all clinical samples by our modification of the technique of Chomczynski and Sacchi which originally described the use of acid guanidinium thiocyanate-phenol-chloroform to preferentially extract RNA from cells and tissues. We replaced room temperature cell lysis by boiling lysis, and acid guanidinium thiocyanate-phenol-chloroform extraction by alkaline phenol-guanidine thiocyanate to preferentially extract DNA from cells. 1.5 ml Sarsted (Newton, N.C.) polypropylene screw cap tubes with o-ring seals were used for the extractions. 200 ul of specimen was added to 500 ul of GPT reagent (6 M guanidine thiocyanate dissolved in 50 mM tris pH 8.3 mixed with an equal volume of phenol buffered in tris pH 8.0). This was mixed by vortexing and immediately placed in a boiling water bath for 15 minutes. The tubes were spun in a microcentrifuge for 5 seconds and 250 ul of chloroform/isoamyl alcohol (24:1 by volume) was added and mixed by vortexing. The liquid phases were separated by centrifugation for 10 minutes and 450 ul of aqueous (upper) phase was transferred to a fresh tube. The aqueous phase was mixed with 500 ul of 100% isopropanol and placed at −20° C. for at least 1 hour. At the end of this period the tubes were centrifuged for 15 minutes and the supernatant removed without disturbing the nucleic acid pellet. The pellet was washed with 500 ul of ice-cold 70% ethanol to remove traces of GPT reagent by gently inverting 2 times and then centrifuged for 5 minutes. The ethanol was removed and the pellet dried in a speed vac for 10 minutes. The pellet was resuspended in 25 ul of sterile deionized water and 5 ul was used in a 50 ul PCR amplification. The PCR was carried out as a hot-start reaction using the thermal cycling conditions for probes SEQ ID NO: 1 and SEQ ID NO: 2 described in example 1. Gel electrophoresis showed that probes SEQ ID NO: 1 and SEQ ID NO: 2 successfully amplified DNA from all 44 specimens.

The amplified DNA from each specimen was transferred to a positively charged polysulphone based membrane. We No false positives were observed, indicating a specificity of 100% for these 4 probes in the clinical specimens tested. 10 out of 12 culture positive samples for *Aspergillus fumigotus*, and 11 out of 13 samples of *Candida albicans* were identified, indicating a detection sensitivity of about 85% for these two probes. Additionally, two out of two *Coccidioides immitis* and two out of two *Cryptococcus neoformans* were correctly identified (detection sensitivity of 100%). As seen by these results, the probes described in this invention can be used on a diverse variety of clinical specimens with excellent efficacy.

TABLE 8

Detection of *Aspergillus fumigatus, Candida albicans, Coccidioides immitis* and *Cryptococcus neoformans* in clinical specimens using species specific probes.

| Specimen type | Smear and culture results | PCR with SEQ ID: 1, 2 | SEQ ID: 3 | SEQ ID: 5 | SEQ ID: 6 | SEQ ID: 7 |
|---|---|---|---|---|---|---|
| U035 sputum | A. flavus | + | − | − | − | − |
| U069 pleura | A. fumigatus | + | + | − | − | − |
| U070 bronchial wash | A. flavus | + | − | − | − | − |
| M019 bronchial wash | A. fumigatus | + | + | − | − | − |
| M020 sputum | mixed fungal flora | + | − | + | − | − |
| X35254 sputum | C. albicans | + | − | + | − | − |
| M20910 sputum | A. fumigatus | + | + | − | − | − |
| M055 sputum | C. albicans | + | − | + | − | − |
| M056 abdominal | mixed fungal flora | + | − | − | − | − |
| M057 drainage tube | C. albicans | + | − | (−) | − | − |
| M059 ind. sputum | C. albicans | + | − | + | − | − |
| M060 ind. sputum | mixed fungal flora | + | − | − | − | − |
| M083 bronchial wash | C. albicans | + | − | + | − | − |
| M084 sputum | A. fumigatus | + | (−) | − | − | − |
| M085 throat | C. albicans | + | − | (−) | − | − |
| A001 sputum | A. fumigatus | + | (−) | − | − | − |
| A002 leg | Blastomyces | + | − | − | − | − |
| A003 leg | Blastomyces | + | − | − | − | − |
| A005 disc | A. fumigatus | + | + | − | − | − |
| A037 disc | A. fumigatus | + | + | − | − | − |
| A039 trachea | C. albicans | + | − | + | − | − |
| A040 trachea | C. albicans | + | − | + | − | − |
| A102 empyema | A. fumigatus | + | + | − | − | − |
| Y004 sputum | C. albicans | + | − | + | − | − |
| Y016 induced sputum | Coccidioides | + | − | − | + | − |
| Y028 sputum | Coccidioides | + | − | − | + | − |
| J003 chest | Aspergillus sp. | + | − | − | − | − |
| J045 bronchial wash | C. albicans | + | − | + | − | − |
| J046 ethmoid | yeast | + | − | − | − | − |
| J047 chest | A. fumigatus | + | + | − | − | − |
| J048 sputum | C. albicans | + | − | + | − | − |
| J073 lung | Aspergillus sp. | + | − | − | − | − |
| J074 lung | A. fumigatus | + | + | − | − | − |
| U017 lip | A. fumigatus | + | + | − | − | − |
| U033 sputum | mixed fungal flora | + | − | − | − | − |
| U071 sputum | C. albicans | + | − | + | − | − |
| U072 BA lavage | Sporothrix | + | − | − | − | − |
| U073 knee | Histoplasma | + | − | − | − | − |
| U074 mandible | Cryptococcus | + | − | − | − | + |
| U075 CSF | Cryptococcus | + | − | − | − | + |
| U076 knee | Histoplasma | + | − | − | − | − |
| U077 soft tissue | Histoplasma | + | − | − | − | − |
| U051 buccal | A. fumigatus | + | + | − | − | − |
| Y055 sputum | mixed fungal flora | + | − | − | − | − |
| + Positive | − Negative | (−) Missed | | | | | radioactively labeled our species specific probes SEQ ID NO: 3, SEQ ID NO: 5, SEQ ID NO: 6 and SEQ ID NO: 7, and sequentially probed the membrane to test for the presence of 28S rDNA from *Aspergillus fumigatus, Candida albicans, Coccidioides immitis* and *Cryptococcus neoformans* respectively. Membrane blocking, probe hybridization and washes were done exactly as described in example 1. The results are shown in Table 8.

EXAMPLE 3

DNA Sequence Based Identification of Unknown Fungal Organisms.

Another utility of our probes is in the rapid DNA sequence based identification of a pure culture of fungus. Probes SEQ ID NO: 1 and SEQ ID NO: 2 are used in a polymerase chain reaction to amplify 28S rDNA from an unknown fungus. Probes SEQ ID NO: 1 or SEQ ID NO: 2 are then used as sequencing primers to obtain DNA sequence from this amplified 28S DNA belonging to the unknown fungus. This DNA sequence is compared to the fungal 28S DNA sequences in our database, and a sequence match at, or overlapping any one of the probe sequences in SEQ ID NO: 3 to SEQ ID NO: 74 will confirm the identity of the fungus. This technique cannot be used directly on clinical samples, as these usually contain DNA from more than one fungus, and the DNA sequence generated will consist of overlapping sequences of several organisms. This technique has utility in rapidly and reliably identifying colonies of a single fungus on culture plates, clinical specimens, food, pharmaceutical, environmental or other samples containing only one species of fungus.

EXAMPLE 4
Capture and Identification of Target DNA or RNA

All primers and probes described in this invention disclosure may be labeled with any detectable reporter or signal moiety including, but not limited to radioisotopes, enzymes, antigens, antibodies, chemiluminescent reagents and fluorescent chemicals. Additionally, these probes may be modified without changing the substance of their purpose by terminal addition of nucleotides designed to incorporate restriction sites or other useful sequences. These probes may also be modified by the addition of a capture moiety (including, but not limited to para-magnetic particles, biotin, fluorescein, dioxigenin, antigens, antibodies) or attached to the walls of microtiter trays to assist in the solid phase capture and purification of these probes and any DNA or RNA hybridized to these probes. Fluorescein may be used as a signal moiety as well as a capture moiety, the latter by interacting with an anti-fluorescein antibody.

A typical utility of these modifications would be as follows. Primers SEQ ID NO: 1 and SEQ ID NO: 2 would be utilized to amplify 28S rDNA from a sample, if present, as described previously. Primers would be modified so as to contain a biotin moiety at their 5' ends. A streptavidin solid phase, such as a paramagnetic particle, would be used to separate PCR products, if present, from the reaction mixture. The amplified target may be subsequently hybridized to a third probe ((SEQ ID NO: 3) to (SEQ ID NO: 74) or their complements) attached to a detectable moiety to determine which species of fungus is present in the given sample. Multiple probes, each labeled with a different detectable moiety may be used at one time to analyze the amplified target.

Alternatively, Primers SEQ ID NO: 1 and SEQ ID NO: 2 would be utilized to amplify 28S rDNA from a sample, if present, as above. In a separate reaction, individually, either SEQ ID NO: 1 or SEQ ID NO: 2 would be modified by attachment to a solid phase capture moiety, such as a paramagnetic particle, and SEQ ID NO: 3 to SEQ ID NO: 74 (or their complements) would be modified by addition of a detectable moiety. Alternately, in the amplicon, any sequences delimited by SEQ ID NO: 1 and SEQ ID NO: 2, including but not limited to SEQ ID NO: 3 to SEQ ID NO: 74, may be used in the design of a capture probe. One of the probes attached to a solid phase (SEQ ID NO: 1 and SEQ ID NO: 2) or any other appropriately designed sequences and one of the probes modified by attachment to a detectable moiety (SEQ ID NO: 3 to SEQ ID NO: 74 or their complements) would be hybridized together, in solution, to products of the PCR, if they had been generated. The hybrids, if present, would be captured from the solution, and analyzed by a method appropriate to the detection moiety. Detection of the hybridized probe would indicate which species of fungus was present in the given sample. Multiple probes, each labeled with a different detectable moiety may be used at one time to analyze the amplified target.

EXAMPLE 5
Species-specific Amplification of Fungal DNA

Another utility of the probes described in this invention is their usage as primers in the direct detection of a specific fungal species by virtue of a nucleic acid amplification reaction. In this embodiment, one primer is a universal one, such as (SEQ ID NO:1) or (SEQ ID NO:2), and the other is a species-specific primer selected from the group consisting of (SEQ ID NO:3) to (SEQ ID NO: 23) or the complements thereof. One variation of this approach is the substitution of (SEQ ID NO:1) or (SEQ ID NO:2) with any functional sequence located in proximity to the species-specific primer. Another variation of this approach is the selection of any appropriate species specific primer pair from SEQ ID NO: 24 to SEQ ID NO: 74.

---

What is claimed is:

1. In a method of DNA extraction wherein the improvement comprises, (a) cell lysis and DNA extraction by boiling cells in an alkaline phenol/guanidine thiocyanate solution.

2. The method of claim 1, wherein isolating the DNA further comprises:

(b) extracting the DNA by the addition of chloroform/isoamyl alcohol.

3. The method of claim 2, wherein isolating the DNA further comprises:

(c) precipitating the DNA by the addition of isopropanol.

4. The method of claim 3, wherein isolating the DNA further comprises:

(d) pelleting the precipitated DNA by centrifugation and washing the pellet with ethanol.

5. In a method of DNA extraction wherein the improvement comprises, (a) cell lysis and DNA extraction by boiling cells in a solution of about 6 M guanidine thiocyanate, 50 mM tris pH 8.3, and an equal volume of phenol buffered in tris pH 8.0 solution.

6. The method of claim 5, wherein isolating the DNA further comprises:

(b) extracting the DNA by the addition of chloroform/isoamyl alcohol (24:1 by volume).

7. The method of claim 6, wherein isolating the DNA further comprises:

(c) precipitating the DNA by the addition of 100% isopropanol and incubating at −20° C. for at least 1 hour.

8. The method of claim 7, wherein isolating the DNA further comprises:

(d) pelleting the precipitated DNA by centrifugation and washing the pellet with ice-cold 70% ethanol.

* * * * *

UNITED STATES PATENT AND TRADEMARK OFFICE
CERTIFICATE OF CORRECTION

PATENT NO. : 5,958,693
DATED : September 28, 1999
INVENTOR(S) : Sandhu et al.

It is certified that error appears in the above-identified patent and that said Letters Patent is hereby corrected as shown below:

Column 1,
Line 58, delete "fingal" and insert in its place -- fungal --.

Column 2,
Line 3, delete "fingi" and insert in its place -- fungi --.
Line 59, delete "Cryprococcus" and insert in its place -- Cryptococcus --.

Column 3,
Line 5, delete "thiis" and insert in its place -- this --.
Line 16, delete "Immunocomprormised" and insert in its place -- Immunocompromised --.
Line 16, delete "hemtogenous" and insert in its place -- hematogenous --.
Line 23, delete "seciation" and insert in its place -- speciation --.
Line 28, delete "polymense" and insert in its place -- polymerase --.

Column 5,
Line 19, delete "fingal" and insert in its place -- fungal --.

Column 6,
Line 47, italicize "Acremonium sp.".
Line 54, italicize "Chrysosporium".
Line 54, italicize "Cladosporium sp.".
Line 55, italicize "Cryptococcus neoformans".
Line 56, italicize "Curvularia", "Geotrichum", and "Mucor".
Line 57, italicize "Penicillium".

Column 8,
Lines 57, 61, 62, 65, 66, and 67, italicize "Acremonium", "Beauvaria", "Bipolaris", "Blastoschizomyces", "Chrysosporium", "Cladosporium", "Cryptococcus neoformans", "Cryptococcus neoformans var. gattii", and "Cryptococcus".

Column 9,
Lines 1, 2, and 3, italicize "terreus", "Curvularia", "Filobasidiella (Cryptococcus) neoformans var bacillispora", and "Filobasidiella (Cryptococcus) neoformans var neoformans".
Lines 5, 6, and 7, italicize "Fusairum", "Geotrichum", "Malbranchea," "Mucor", "Paecilomyces", "Penicillium", and "Rhizopus".
Table 2, line 21, of the entries in the table, delete the duplicate entry of "Candida krusel".
Table 2, line 25, of the entries in the table, delete "Chrysosponum sp." and insert in its place -- Chrysosporium --.
Table 2, line 35, of the entries in the table, delete "Fiolbasidiella" and insert in its place -- Filobasidiella --.

UNITED STATES PATENT AND TRADEMARK OFFICE
CERTIFICATE OF CORRECTION

PATENT NO. : 5,958,693
DATED : September 28, 1999
INVENTOR(S) : Sandhu et al.

It is certified that error appears in the above-identified patent and that said Letters Patent is hereby corrected as shown below:

Column 11,
Lines 33-34, delete "neoforntans" and insert in its place -- neoformans --.
Lines 29, 30, 31, 32, and 34, italicize "Cryptococcus neoformans", "Cryptococcus neoformans", "gatii", "Filobasidiella (Cryptococcus) neoformans", "bacillispora", Filobasidiella (Cryptococcus) neoformans", and "neoformans".
Line 44, delete "fmal" and insert in its place -- final --.

Column 12,
Line 42, delete "amplifmg" and insert in its place -- amplifying --
Line 2, delete "timne" and insert in its place -- time --
Line 42, delete "fuingi" and insert in its place -- fungi --.

Column 23,
Approximately line 55, delete "usfus" and insert in its place -- ustus --.

Column 24,
Line 58, delete "Hybridization Specificilty" and insert in its place -- hybridization specificity --.
Line 64, italicize "Acremonium".

Column 25,
Lines 1, 5, 6, 7, 8, and 9, italicize "Aspergillus", "Beauvaria", "Bipolaris", "Chrysosporium", "Cladosporium", "Cryptococcus neoformans", "Curvularia", "Fusarium", "Geotrichum", "Mucor", "Penicillium", and "Rhizopus".

Column 26,
Line 3, delete "fumgi" and insert in its place -- fungi --.

Column 27,
Table 3, line 14, under the heading "Fungus", delete "Bipoiaris" and insert in its place -- Bipolaris --.

Column 27,
Table 3, line 26, under the heading "Fungus", delete "Coccidiodides" and insert in its place -- Coccidioides --.
Table 3, line 37, under the heading "Fungus", delete "brevicauiis" and insert in its place -- brevicaulis --.

UNITED STATES PATENT AND TRADEMARK OFFICE
CERTIFICATE OF CORRECTION

PATENT NO. : 5,958,693
DATED : September 28, 1999
INVENTOR(S) : Sandhu et al.

It is certified that error appears in the above-identified patent and that said Letters Patent is hereby corrected as shown below:

Column 27,
Table 4, line 14, under the heading "Fungus", delete "Bipoiaris" and insert in its place -- Bipolaris --.

Column 29,
Table 4, line 16, under the heading "Fungus", delete "Pseudilescheria" and insert in its place -- Pseudallescheria --.

Column 29,
Table 4, line 19, under the heading "Fungus", delete "brevicauiis" and insert in its place -- brevicaulis --.

Column 29,
Table 5, line 4, under the heading "SEQ ID: 15", delete "+" and insert in its place -- - --.

Column 29,
Table 5, line 14, under the heading "Fungus", delete "Bipoiaris" and insert in its place -- Bipolaris --.

Column 31,
Table 5, line 1, under the heading "Fungus", delete "brevicauiis" and insert in its place -- brevicaulis --

Column 31,
Table 6, lines 2 and 3, under the heading "Fungus", delete both occurrences of "Aspergllus" and insert in their place -- Aspergillus --.

Column 32,
Table 6, line 30, delete "capsuiatum" and insert in its place -- capsulatum --.
Table 6, line 37, delete "Scopitlariopsis" and insert in its place -- Scopulariopsis --.

Column 32,
Table 6, approximately line 40, delete "Thichosporon" and insert in its place -- Trichosporon --.

UNITED STATES PATENT AND TRADEMARK OFFICE
CERTIFICATE OF CORRECTION

PATENT NO. : 5,958,693
DATED : September 28, 1999
INVENTOR(S) : Sandhu et al.

It is certified that error appears in the above-identified patent and that said Letters Patent is hereby corrected as shown below:

Column 36,
Line 4, delete "fumigotus" and insert in its place -- fumigatus --.

Signed and Sealed this

Twenty-ninth Day of January, 2002

Attest:

Attesting Officer

JAMES E. ROGAN
Director of the United States Patent and Trademark Office

SEQUENCE LISTING (1) GENERAL INFORMATION:

(iii) NUMBER OF SEQUENCES: 78

(2) INFORMATION FOR SEQ ID NO:1:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "probe for fungal organisms"

(xi) SEQUENCE DESCRIPTION: SEQ ID NO:1:

GTGAAATTGT TGAAAGGGAA                                              20

(2) INFORMATION FOR SEQ ID NO:2:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "probe for fungal organisms"

(xi) SEQUENCE DESCRIPTION: SEQ ID NO:2:

GACTCCTTGG TCCGTGTT                                                  18

(2) INFORMATION FOR SEQ ID NO:3:

(i) SEQUENCE CHARACTERISTICS:
    (A) LENGTH: 14 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "probe for Aspergillus
        fumigatus"

(xi) SEQUENCE DESCRIPTION: SEQ ID NO:3:

CTCGGAATGT ATCA                                                      14

(2) INFORMATION FOR SEQ ID NO:4:

(i) SEQUENCE CHARACTERISTICS:
    (A) LENGTH: 13 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "probe for Blastomyces
        dermatitidis"

(xi) SEQUENCE DESCRIPTION: SEQ ID NO:4:

ACTCCCCCAC GGG                                                       13

(2) INFORMATION FOR SEQ ID NO:5:

(i) SEQUENCE CHARACTERISTICS:
    (A) LENGTH: 14 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "probe for Candida albicans"

(xi) SEQUENCE DESCRIPTION: SEQ ID NO:5:

CCTCTGACGA TGCT                                                      14

(2) INFORMATION FOR SEQ ID NO:6:

(i) SEQUENCE CHARACTERISTICS:
    (A) LENGTH: 14 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "probe for Coccidioides
        immitis"

(xi) SEQUENCE DESCRIPTION: SEQ ID NO:6:

TCTGGCGGTT GGTT                                                      14

(2) INFORMATION FOR SEQ ID NO:7:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe for Cryptococcus
            neoformans"

(xi) SEQUENCE DESCRIPTION: SEQ ID NO:7:

CTCCTGTCGC ATAC                                          14

(2) INFORMATION FOR SEQ ID NO:8:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe for Cryptococcus
            neoformans"

(xi) SEQUENCE DESCRIPTION: SEQ ID NO:8:

AGTTCTGATC GGTG                                          14

(2) INFORMATION FOR SEQ ID NO:9:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe for Histoplasm
            capsulatum"

(xi) SEQUENCE DESCRIPTION: SEQ ID NO:9:

CAATCCCCCG CGGC                                          14

(2) INFORMATION FOR SEQ ID NO:10:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe for Aspergillus
            glaucus"

(xi) SEQUENCE DESCRIPTION: SEQ ID NO:10:

GTGTCATGCG GCCA                                          14

(2) INFORMATION FOR SEQ ID NO:11:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe for Aspergillus -continued niger"

(xi) SEQUENCE DESCRIPTION: SEQ ID NO:11:

CCCTGGAATG TAGT                                                    14

(2) INFORMATION FOR SEQ ID NO:12:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "prober for Aspergillus
            terreus"

(xi) SEQUENCE DESCRIPTION: SEQ ID NO:12:

GCTTCGGCCC GGTG                                                    14

(2) INFORMATION FOR SEQ ID NO:13:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe for Candida glabrata"

(xi) SEQUENCE DESCRIPTION: SEQ ID NO:13:

CTTGGGACTC TCGC                                                    14

(2) INFORMATION FOR SEQ ID NO:14:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe for Candida
            guilliermondii"

(xi) SEQUENCE DESCRIPTION: SEQ ID NO:14:

ATATTTTGTG AGCC                                                    14

(2) INFORMATION FOR SEQ ID NO:15:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe for Candida Kefyr"

(xi) SEQUENCE DESCRIPTION: SEQ ID NO:15:

TTCGGCTTTC GCTG                                                    14

(2) INFORMATION FOR SEQ ID NO:16:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe for Candida krusei"

(xi) SEQUENCE DESCRIPTION: SEQ ID NO:16:

GGGATTGCGC ACCG                                                              14

(2) INFORMATION FOR SEQ ID NO:17:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe for Candida
             lusitaniae"

(xi) SEQUENCE DESCRIPTION: SEQ ID NO:17:

GCCTCCATCC CTTT                                                              14

(2) INFORMATION FOR SEQ ID NO:18:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe for Candida
             parapsilosis"

(xi) SEQUENCE DESCRIPTION: SEQ ID NO:18:

ATAAGTGCAA AGAA                                                              14

(2) INFORMATION FOR SEQ ID NO:19:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe for Candida
             tropicalis"

(xi) SEQUENCE DESCRIPTION: SEQ ID NO:19:

AGAATTGCGT TGGA                                                              14

(2) INFORMATION FOR SEQ ID NO:20:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe for Pseudallescheria
             boydii"

(xi) SEQUENCE DESCRIPTION: SEQ ID NO:20:

GCGATGGGAA TGTG                                                              14

(2) INFORMATION FOR SEQ ID NO:21:

(i) SEQUENCE CHARACTERISTICS:

(A) LENGTH: 14 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "probe for Aspergillus
                flavus"

(xi) SEQUENCE DESCRIPTION: SEQ ID NO:21:

AGACTCGCCT CCAG                                                              14

(2) INFORMATION FOR SEQ ID NO:22:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "probe for Sporothrix
                schenckii"

(xi) SEQUENCE DESCRIPTION: SEQ ID NO:22:

CGGACCACCC GGCG                                                              14

(2) INFORMATION FOR SEQ ID NO:23:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "probe for Sporothrix
                schenckii"

(xi) SEQUENCE DESCRIPTION: SEQ ID NO:23:

CGGCGGCATG CCCC                                                              14

(2) INFORMATION FOR SEQ ID NO:24:

(i) SEQUENCE CHARACTERISTICS:
            (A) LENGTH: 208 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: Acremonium (xi) SEQUENCE DESCRIPTION: SEQ ID NO:24:

GACCAGACTT GGGCTCGGTG AATCATCCGG CGTTCTCGCC GGTGCACTTT GCCGTCCCAG             60

GCCAGCATCA GTTCGCGCCG GGGGATAAAG GTTTCGGGAA TGTAGCTCCT TCGGGAGTGT            120

TATAGCCCGT TGCGTAATAC CCTGGCGTGG ACTGAGGTCC GCGCTCTGCA AGGATGCTGG            180

CGTAATGGTC ATCAGTGACC CGTCTTGA                                              208

(2) INFORMATION FOR SEQ ID NO:25:

(i) SEQUENCE CHARACTERISTICS:
            (A) LENGTH: 212 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
        (A) ORGANISM: Aspergillus clavatus (xi) SEQUENCE DESCRIPTION: SEQ ID NO:25:

```
GACCAGACTC GCTCGCGGGG TTCAGCCGGC ATTCGTGCCG GTGTACTTCC CCGTGGGCGG      60

GCCAGCGTCG GTTTGGGCGG CCGGTCAAAG GCCTCCGGAA TGTATCACCT CTCGGGGTGT     120

CTTATAGCCG GGGGTGCAAT GCGGCCTGCC TGGACCGAGG AACGCGCTTC GGCTCGGACG     180

CTGGCGTAAT GGTCGTAAAT GACCCGTCTT GA                                   212
```

(2) INFORMATION FOR SEQ ID NO:26:

(i) SEQUENCE CHARACTERISTICS:
        (A) LENGTH: 212 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Aspergillus flavus (xi) SEQUENCE DESCRIPTION: SEQ ID NO:26:

```
GACCAGACTC GCCTCCAGGG TTCAGCCGGC ATTCGTGCCG GTGTACTTCC CTGGGGCGG       60

GCCAGCGTCG GTTTGGGCGG CCGGTCAAAG GCTCCCGGAA TGTAGTGCCC TYCGGGGCAC     120

CTTATAGCCG GGAGTGCAAT GCGGCCAGCC TGGACCGAGG AACGCGCTTC GGCACGGACG     180

CTGGCATAAT GGTCGYAAAC GACCCGTCTT GA                                   212
```

(2) INFORMATION FOR SEQ ID NO:27:

(i) SEQUENCE CHARACTERISTICS:
        (A) LENGTH: 212 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Aspergillus fumigatus (xi) SEQUENCE DESCRIPTION: SEQ ID NO:27:

```
GACCAGACTC GCCCGCGGGG TTCAGCCGGC ATTCGTGCCG GTGTACTTCC CCGTGGGCGG      60

GCCAGCGTCG GTTTGGGCGG CCGGTCAAAG GCCCTCGGAA TGTATCACCT CTCGGGGTGT     120

CTTATAGCCG AGGGTGCAAT GCGGCCTGCC TGGACCGAGG AACGCGCTTC GGCTCGGACG     180

CTGGCGTAAT GGTCGTAAAT GACCCGTCTT GA                                   212
```

(2) INFORMATION FOR SEQ ID NO:28:

(i) SEQUENCE CHARACTERISTICS:
        (A) LENGTH: 212 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Aspergillus glaucus (xi) SEQUENCE DESCRIPTION: SEQ ID NO:28:

```
GACCAGACTC GCTTCCGGGG TTCAGCCGGC TTTCGGGCCG GTGTACTTCC CCGGGGGCGG      60
```

```
GCCAGCGTCG GTTTGGGCGG CCGGTCAAAG GCCCCTGGAA TGTAACGCCT CTCGGGGCGC        120

CTTATAGCCA GGGGTGTCAT GCGGCCAGCC TGGACCGAGG AACGCGCTTC GGCACGGACG        180

CTGGCATAAT GGTCGTAAAC GACCCGTCTT GA                                     212

(2) INFORMATION FOR SEQ ID NO:29:

(i) SEQUENCE CHARACTERISTICS:
        (A) LENGTH: 213 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Aspergillus nidulans (xi) SEQUENCE DESCRIPTION: SEQ ID NO:29:

GACCAGACTC GGCCCCGGGG TTCARCCAGC ACTCGTGCTG GTGTACTTCC CCGGGGGCGG         60

GCCAGCGTCG GTTTGGGCGG CCGGTCAAAG GCCCCAGGAA TGTATCGCCC TCCGGGGTTG        120

TCTTATAGCC TGGGGTGCAA TGCGGCCAGC CCGGACCGAG GAACGCGCTT CGGCACGGAC        180

GCTGGCGTAA TGGTCGCAAA CGACCCGTCT TGA                                    213

(2) INFORMATION FOR SEQ ID NO:30:

(i) SEQUENCE CHARACTERISTICS:
        (A) LENGTH: 212 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Aspergillus niger (xi) SEQUENCE DESCRIPTION: SEQ ID NO:30:

GACCAGACTC GCCCGCGGGG TTCAGCCGGC ATTCGTGCCG GTGTACTTCC CCGTGGGCGG         60

GCCAGCGTCG GTTTGGGCGG CCGGTCAAAG GCCCCTGGAA TGTAGTRCCC TCCGGGGYAC        120

CTTATAGCCA GGGGTGCAAT GCGGCCAGCC TGGACCGAGG AACGCGCTTC GGCACGGACG        180

CTGGCATAAT GGTCGTAAAC GACCCGTCTT GA                                     212

(2) INFORMATION FOR SEQ ID NO:31:

(i) SEQUENCE CHARACTERISTICS:
        (A) LENGTH: 212 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Aspergillus ochraceus (xi) SEQUENCE DESCRIPTION: SEQ ID NO:31:

GACCAGACTC GCCCGCGGGG TTCAGCCGGC ATTCGTGCCG GTGTACTTCC CCGCGGGCGG         60

GCCAGCGTCG GTTTGGGCGG CCGGTCAAAG GCCCCCGGAA TGTAGCACCC TTCGGGGTGC        120

CTTATAGCCG GGGGTGCAAT GCGGCCAGCC TGGACCGAGG AACGCGCTTC GGCACGGACG        180

CTGGCATAAT GGTCGTAAAC GACCCGTCTT GA                                     212
```

(2) INFORMATION FOR SEQ ID NO:32:

(i) SEQUENCE CHARACTERISTICS:
        (A) LENGTH: 212 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Aspergillus terreus (xi) SEQUENCE DESCRIPTION: SEQ ID NO:32:

```
AACCAGACTC GCTCGCGGGG TTCAGCCGGG CTTCGGCCCG GTGTACTTCC CCGCGGGCGG      60

GCCAGCGTCG GTTTGGGCGG CCGGTCAAAG GCCTCCGGAA TGTAGCGCCC TTCGGGGCGC     120

CTTATAGCCG GGGGTGCAAT GCGGCCAGCC TGGACCGAGG AACGCGCTTC GGCACGGACG     180

CTGGCATAAT GGTTGTAAAC GACCCGTCTT GA                                   212
```

(2) INFORMATION FOR SEQ ID NO:33:

(i) SEQUENCE CHARACTERISTICS:
        (A) LENGTH: 213 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Aspergillus ungius (xi) SEQUENCE DESCRIPTION: SEQ ID NO:33:

```
GACCAGACTC GGCCTCGGGG TTCAGCCAGC ACTCGTGCTG GTGTACTTCC CCGGGGCGG       60

GCCAGCGTCG GTTTGGGCGG CCGGTCAAAG GCCCCAGGAA TGTATCACCC TCCGGGGTTG    120

TCTTATAGCC TGGGGTGCAA TGCGGCCAGC CTGGACCGAG GAACGCGCTT CGGCACGGAC    180

GCTGGCATAA TGGTTGCAAA CGACCCGTCT TGA                                 213
```

(2) INFORMATION FOR SEQ ID NO:34:

(i) SEQUENCE CHARACTERISTICS:
        (A) LENGTH: 212 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Aspergillus ustus (xi) SEQUENCE DESCRIPTION: SEQ ID NO:34:

```
GACCAGACTC GGCCCCGGGG TTCAGCCAGC ACTCGTGCTG GTGTACTTCC CCGGGGCGG       60

GCCAGCGTCG GTTTGGGCGG CCGGTCAAAG GCCCCAGGAA TGTGTCGCCC TCCGGGGCGT    120

CTTATAGCCT GGGGTGCAAT GCGGCCAGCC CGGACCGAGG AACGCGCTTC GGCACGGACG    180

CTGGCGTAAT GGTCGCAAAC GACCCGTCTT GA                                  212
```

(2) INFORMATION FOR SEQ ID NO:35:

(i) SEQUENCE CHARACTERISTICS:
        (A) LENGTH: 208 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
    (A) ORGANISM: Beauveria (xi) SEQUENCE DESCRIPTION: SEQ ID NO:35:

```
GACCAGACTT GGGCTTGGTT GATCATCCGG GGTTCTCCCC GGTGCACTCT TCCGGCCCAG        60

GCCAGCATCA GTTCGCCCTG GGGGACAAAG GCTTCGGGAA CGTGGCTCTC TCCGGGGAGT       120

GTTATAGCCC GTTGCGTAAT ACCCTGTGGC GGACTGAGGT TCGCGCATTC GCAAGGATGC       180

TGGCGTAATG GTCATCAGTG ACCCGTCT                                          208
```

(2) INFORMATION FOR SEQ ID NO:36:

(i) SEQUENCE CHARACTERISTICS:
        (A) LENGTH: 213 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Bipolaris (xi) SEQUENCE DESCRIPTION: SEQ ID NO:36:

```
AGCCAGACTT GCTTGCAGTT GCTCATCCGG GCTTTTGCCC GGTGCACTCT TCTGCAGGCA        60

GGCCAGCATC AGTTTGGGCG GTGGGATAAA GGTCTCTGTC ACGTACCTTC CTTCGGGTTG       120

GCCATATAGG GGAGACGTCA TACCACCAGC CTGGACTGAG GTCCGCGCAT CTGCTAGGAT       180

GCTGGCGTAA TGGCTGTAAG CGGCCCGTCT TGA                                    213
```

(2) INFORMATION FOR SEQ ID NO:37:

(i) SEQUENCE CHARACTERISTICS:
        (A) LENGTH: 105 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Blastoschizomyces (xi) SEQUENCE DESCRIPTION: SEQ ID NO:37:

```
TGAAATTGTT GAAAGGGAAG GCGATGGTAG GAATAAGAGG CTGCGGTTTG AAATAATTGT        60

TTTTCGGGCC ACGGTCTCCT GAGCCTGCTT TCGCACCCGT CTTGA                       105
```

(2) INFORMATION FOR SEQ ID NO:38:

(i) SEQUENCE CHARACTERISTICS:
        (A) LENGTH: 214 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Blastomyces dermatitidis (xi) SEQUENCE DESCRIPTION: SEQ ID NO:38:

```
GACCAGAGTC GGCCGTGGGG GTTCAGCGGG CATTCGTTGC CCGTGCACTC CCCCACGGGC        60

GGGCCAGCGT CGGTTTCGAC GGCCGGTCAA AGGCCCCCGG AATGTGTCGC CTCTCGGGGC       120

GTCTTATAGC CGGGGGTGCA ATGCGGCCAG TCGGGACCGA GGAACGCGCT TCGGCACGGA       180
```

```
CGCTGGCTTA ATGGTCGTAA GCGACCCGTC TTGA                              214
```

(2) INFORMATION FOR SEQ ID NO:39:

(i) SEQUENCE CHARACTERISTICS:
        (A) LENGTH: 213 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Chrysosporium (xi) SEQUENCE DESCRIPTION: SEQ ID NO:39:

```
AACCAGACTT GCGCGCGGCC GATCATCCGG TGTTCTCACC GGTGCACTCG GCCGTGCTCA    60

GGCCAGCATC GGTTTTGGCG GCTGGATAAA GGCCCTAGGA ATGTGGCTCC TCTCGGGGAG   120

TGTTATAGCC TAGGGTGCAA TGCAGCCTGC TGGGACCGAG GACCGCGCTT CGGCTAGGAT   180

GCTGGCGTAA TGGTTGTAAG CGGCCCGTCT TGA                                213
```

(2) INFORMATION FOR SEQ ID NO:40:

(i) SEQUENCE CHARACTERISTICS:
        (A) LENGTH: 207 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Cladosporium (xi) SEQUENCE DESCRIPTION: SEQ ID NO:40:

```
AACCAGACTT GCTCGCGGTG TTCCGCCGGT CTTCTGACCG GTCTACTCGC CGCGTTGCAG    60

GCCAGCATCG TCTGGTGCCG CTGGATAAGA CTTGAGGAAT GTAGCTCCCT CGGGAGTGTT   120

ATAGCCTCTT GTGATGCAGC GAGCGCCGGG CGAGGTCCGC GCTTCGGCTA GGATGCTGGC   180

GTAATGGTCG TAATCCGCCC GTCTTGA                                       207
```

(2) INFORMATION FOR SEQ ID NO:41:

(i) SEQUENCE CHARACTERISTICS:
        (A) LENGTH: 213 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Curvularia (xi) SEQUENCE DESCRIPTION: SEQ ID NO:41:

```
AGCCAGACTT GCTTGCAGTT GCTCATCCGG GCTTTTGCCC GGTGCACTCT TCTGCAGGCA    60

GGCCAGCATC AGTTTGGGCG GTGGGATAAA GGTCTCTGAC ACGTTCCTTC CTTCGGGTTG   120

GCCATATAGG GGAGACGTCA TACCACCAGC CTGGACTGAG GTCCGCGCAT CTGCTAGGAT   180

GCTGGCGTAA TGGCTGTAAG CGGCCCGTCT TGA                                213
```

(2) INFORMATION FOR SEQ ID NO:42:

(i) SEQUENCE CHARACTERISTICS:
        (A) LENGTH: 213 base pairs

```
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Candida albicans (xi) SEQUENCE DESCRIPTION: SEQ ID NO:42:

GATCAGACTT GGTATTTTGC ATGCTGCTCT CTCGGGGCG GCCGCTGCGG TTTACCGGGC      60

CAGCATCGGT TTGGAGCGGC AGGATAATGG CGGAGGAATG TGGCACGGCT TCTGCTGTGT    120

GTTATAGCCT CTGACGATGC TGCCAGCCTA GACCGAGGAC TGCGGTTTTT AACCTAGGAT    180

GTTGGCATAA TGATCTTAAG TCGCCCGTCT TGA                                 213

(2) INFORMATION FOR SEQ ID NO:43:

(i) SEQUENCE CHARACTERISTICS:
        (A) LENGTH: 223 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Candida glabrata (xi) SEQUENCE DESCRIPTION: SEQ ID NO:43:

GATCAGACAT GGTGTTTTGC GCCCCTTGCC TCTCGTGGGC TTGGGACTCT CGCAGCTCAC     60

TGGGCCAGCA TCGGTTTTGG CGGCCGGAAA AAACCTAGGG AATGTGGCTC TGCGCCTCGG    120

TGTAGAGTGT TATAGCCCTG GGGAATACGG CCAGCCGGGA CCGAGGACTG CGATACTTGT    180

TATCTAGGAT GCTGGCATAA TGGTTATATG CCGCCCGTCT TGA                      223

(2) INFORMATION FOR SEQ ID NO:44:

(i) SEQUENCE CHARACTERISTICS:
        (A) LENGTH: 212 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Candida guilliermondii (xi) SEQUENCE DESCRIPTION: SEQ ID NO:44:

GATCAGACTC GATATTTTGT GAGCCTTGCC TTCGTGGCGG GGTGACCCGC AGCTTATCGG     60

GCCAGCATCG GTTTGGGCGG TAGGATAATG GCGTAGGAAT GTGACTTTRC TTCGGTGAAG    120

TGTTATAGCC TGCGTTGATG CTGCCTGCCT AGACCGAGGA CTGCGATTTT ATCAAGGATG    180

CTGGCATAAT GATCCCAAAC CGCCCGTCTT GA                                  212

(2) INFORMATION FOR SEQ ID NO:45:

(i) SEQUENCE CHARACTERISTICS:
        (A) LENGTH: 214 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Coccidioides immitis
```

(xi) SEQUENCE DESCRIPTION: SEQ ID NO:45:

```
AACCAGACTC GGTCGTGGGG GCTCAGCGGG CATGAGTGCC CGTGTACTCC CCCATGCTCC      60

GGGCCAGCAT CAGTTCTGGC GGTTGGTTAA AGGCCTCTGG AATGTATCGT CCTCCGGGAC     120

GTCTTATAGC CAGGGGCGCA ATGCGGCCAG CCGGGACTGA GGAACGCGCT TCGGCACGGA     180

TGCTGGCATA ATGGTTGTAA GCGGCCCGTC TTGA                                 214
```

(2) INFORMATION FOR SEQ ID NO:46:

(i) SEQUENCE CHARACTERISTICS:
        (A) LENGTH: 187 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Candida kefyr (xi) SEQUENCE DESCRIPTION: SEQ ID NO:46:

```
GATCAGACAT GGCGTTTGCT TCGGCTTTCG CTGGGCCAGC ATCAGTTTTA GCGGTTGGAT      60

AAATCCTCGG GAATGTGGCT CTGCTTCGGT AGAGTGTTAT AGCCCGTGGG AATACAGCCA     120

GCTGGGACTG AGGATTGCGA CTTTTGTCAA GGATGCTGGC GTAATGGTTA AATGCCGCCC     180

GTCTTGA                                                               187
```

(2) INFORMATION FOR SEQ ID NO:47:

(i) SEQUENCE CHARACTERISTICS:
        (A) LENGTH: 213 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Candida krusei (xi) SEQUENCE DESCRIPTION: SEQ ID NO:47:

```
CGCCCGACAT GGGGATTGCG CACCGCTGCC TCTCGTGGGC GGCGCTCTGG GCTTTCCCTG      60

GGCCAGCATC GGTTCTTGCT GCAGGAGAAG GGGTTCTGGA ACGTGGCTCT TCGGAGTGTT     120

ATAGCCAGGG CCAGATGCTG CGTGCGGGGA CCGAGGACTG CGGCCGTGTA GGTCACGGAT     180

GCTGGCAGAA CGGCGCAACA CCGCCCGTCT TGA                                  213
```

(2) INFORMATION FOR SEQ ID NO:48:

(i) SEQUENCE CHARACTERISTICS:
        (A) LENGTH: 236 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Cryptococcus laurentii (xi) SEQUENCE DESCRIPTION: SEQ ID NO:48:

```
AGTCAGTCGT GTCTGGGAGG CTCAGCCGGT TCTGCCGGTG TATTCCTCTC AGACGGGTCA      60

ACATCAGTTT TGTCCGACGG ATAATGGCGG CGGGAAAGTA GCACCTCCGG GTGTGTTATA     120

GCCCGCTGTC GCATACGCCG GATGAGACTG AGGCATGCAG CTCGCCTTTA TGGCAGGGGT     180
```

TCGCCCACTT TCGAGCTTAG GATGTTGACG TAATGGCTTT AAACGACCCG TCTTGA        236

(2) INFORMATION FOR SEQ ID NO:49:

(i) SEQUENCE CHARACTERISTICS:
        (A) LENGTH: 173 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Candida lusitaniae (xi) SEQUENCE DESCRIPTION: SEQ ID NO:49:

AAGCAGACAC GGTTTTACCG GGCCAGCGTC GAAAAGGGGG GAGGAACAAG AACTCGAGAA        60

TGTGGCGCGC ACCTTCGGGY GCGCGTGTTA TAGCTCGTGT TGACGCCTCC ATCCCTTTTC       120

GAGGCCTGCG ATTCTAGGAC GCTGGCGTAA TGGTTGCAAG CCGCCCGTCT TGA             173

(2) INFORMATION FOR SEQ ID NO:50:

(i) SEQUENCE CHARACTERISTICS:
        (A) LENGTH: 238 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Cryptococcus neofomans var gattii (serotype B)

(xi) SEQUENCE DESCRIPTION: SEQ ID NO:50:

AGTCAGTCGT GTCTATTGGG TTCAGCCAGC TCTGCTGGTG TATTCCCTTT AGACGGGTCA        60

ACATCAGTTC TGATCGGTGG ATAAGGGCTG GAGGAATGTG GCACTCTTCG GGGTGTGTTA       120

TAGCCTCCTG TCGCATACAC TGGTTGGGAC TGAGGAATGC AGCTCGCCTT TATGGCCGGG       180

GTTCGCCCAC GTTCGAGCTT AGGATGTTGA CAAAATGGCT TTAAACGACC CGTCTTGA        238

(2) INFORMATION FOR SEQ ID NO:51:

(i) SEQUENCE CHARACTERISTICS:
        (A) LENGTH: 238 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Cryptococcus neoformans (serotype A)

(xi) SEQUENCE DESCRIPTION: SEQ ID NO:51:

AGTCAGTCGT GTCTATTGGG TTCAGCCAGT TCTGCTGGTG TATTCCCTTT AGACGGGTCA        60

ACATCAGTTC TGATCGGTGG ATAAGGGCTG GGGGAATGTA GCACTCTTCG GAGTGTGTTA       120

TAGCCTCCTG TCGCATACAC TGGTTGGGAC TGAGGAATGC AGCTCGCCTT TATGGCCGGG       180

GTTCGCCCAC GTTCGAGCTT AGGATGTTGA CAAAATGGCT TTAAACGACC CGTCTTGA        238

(2) INFORMATION FOR SEQ ID NO:52:

(i) SEQUENCE CHARACTERISTICS:
        (A) LENGTH: 211 base pairs
        (B) TYPE: nucleic acid
        (C) STRANDEDNESS: single -continued (D) TOPOLOGY: linear (ii) MOLECULE TYPE: DNA (genomic)

(vi) ORIGINAL SOURCE:
          (A) ORGANISM: Candida parapsilosis (xi) SEQUENCE DESCRIPTION: SEQ ID NO:52:

GATCAGACTT GGTATTTTGT ATGTTACTCT CTCGGGGGTG GCCTCTACAG TTTACCGGGC        60

CAGCATCAGT TTGAGCGGTA GGATAAGTGC AAAGAAATGT GGCACTGCTT CGGTAGTGTG       120

TTATAGTCTT TGTCGATACT GCCAGCTTAG ACTGAGGACT GCGGCTTCGG CCTAGGATGT       180

TGGCATAATG ATCTTAAGTC GCCCGTCTTG A                                      211

(2) INFORMATION FOR SEQ ID NO:53:

(i) SEQUENCE CHARACTERISTICS:
          (A) LENGTH: 238 base pairs
          (B) TYPE: nucleic acid
          (C) STRANDEDNESS: single
          (D) TOPOLOGY: linear (ii) MOLECULE TYPE: DNA (genomic)

(vi) ORIGINAL SOURCE:
          (A) ORGANISM: Cryptococcus terreus (xi) SEQUENCE DESCRIPTION: SEQ ID NO:53:

AGTCAGTCAT GTCTATTGGA CTCAGCCGGT TCTGCCGGTG TACTTCCTTT AGATGGGGTC        60

AACATCAGTT TTGATCGCTG GAAAAGGGCA GGAGGAATGT AGCACTCTCG GGTGAACTTA       120

TAGCCTTCTG TCGTATACAG TGGTTGGGAC TGAGGAACGC AGCATGCCTT TATGGCCGGG       180

GTTCGCCCAC GTACATGCTT AGGATGTTGA CATAATGGCT TTAAACGACC CGTCTTGA        238

(2) INFORMATION FOR SEQ ID NO:54:

(i) SEQUENCE CHARACTERISTICS:
          (A) LENGTH: 211 base pairs
          (B) TYPE: nucleic acid
          (C) STRANDEDNESS: single
          (D) TOPOLOGY: linear (ii) MOLECULE TYPE: DNA (genomic)

(vi) ORIGINAL SOURCE:
          (A) ORGANISM: Candida tropicalis (xi) SEQUENCE DESCRIPTION: SEQ ID NO:54:

GATCAGACTT GGTATTTTGT ATGTTACTTC TTCGGGGGTG GCCTCTACAG TTTATCGGGC        60

CAGCATCAGT TTGGGCGGTA GGAGAATTGC GTTGGAATGT GGCACGGCTT CGGTTGTGTG       120

TTATAGCCTT CGTCGATACT GCCAGCCTAG ACTGAGGACT GCGGTTTATA CCTAGGATGT       180

TGGCATAATG ATCTTAAGTC GCCCGTCTTG A                                      211

(2) INFORMATION FOR SEQ ID NO:55:

(i) SEQUENCE CHARACTERISTICS:
          (A) LENGTH: 211 base pairs
          (B) TYPE: nucleic acid
          (C) STRANDEDNESS: single
          (D) TOPOLOGY: linear (ii) MOLECULE TYPE: DNA (genomic)

(vi) ORIGINAL SOURCE:
          (A) ORGANISM: Fusarium (xi) SEQUENCE DESCRIPTION: SEQ ID NO:55:

```
GACCAGACTT GGGCTTGGTT AATCATCTGG GGTTCTCYCC AGTGCACTTT TCCAGTCCAG      60

GCCAGCATCA GTTTTCSCCG GGGGATAAAG RCTTCGGGAA TGTGGCTCYC YYCGGGGAGT     120

GTTATAGCCC GTTGYGTAAT ACCCTGGBGG GGACTGAGGT TCGCGCWTCT GCAAGGATGC     180

TGGCGTAATG GTCATCAACG ACCCGTCTTG A                                    211
```

(2) INFORMATION FOR SEQ ID NO:56:

(i) SEQUENCE CHARACTERISTICS:
        (A) LENGTH: 238 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Filobasidium capsuligenum (xi) SEQUENCE DESCRIPTION: SEQ ID NO:56:

```
AGTCAGTCAT GTCTATTGGA CTCAGCCGGT TCTGCCGGTG TATTTCCTTT AGATGGGGTC      60

AACATCAGTT TTGACCGTTG GATAAAGGCA GGAAGAATGT AGCACTCTCG GGTGAACTTA     120

TAGCTTCTTG TCACATACAA TGGTTGGGAC TGAGGAACGC AGCATGCCTT TATGGCCGGG     180

ATTCGTCCAC GTACATGCTT AGGATGTTGA CATAATGGCT TTAAACGACC CGTCTTGA      238
```

(2) INFORMATION FOR SEQ ID NO:57:

(i) SEQUENCE CHARACTERISTICS:
        (A) LENGTH: 238 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Filobasidiella neofomans var bacillispora
            (serotype C)

(xi) SEQUENCE DESCRIPTION: SEQ ID NO:57:

```
AGTCAGTCGT GTCTATTGGG TTCAGCCAGC TCTGCTGGTG TATTCCCTTT AGACGGGTCA      60

ACATCAGTTC TGATCGGTGG ATAAGGGCTG GAGGAATGTG GCACTCTTCG GGGTGTGTTA     120

TAGCCTCCTG TCGCATACAC TGGTTGGGAC TGAGGAATGC AGCTCGCCTT TATGGCCGGG     180

GTTCGCCCAC GTTCGAGCTT AGGATGTTGA CAAAATGGCT TTAAACGACC CGTCTTGA      238
```

(2) INFORMATION FOR SEQ ID NO:58:

(i) SEQUENCE CHARACTERISTICS:
        (A) LENGTH: 238 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Filobasidiella neofomans var neoformans
            (serotype D)

(xi) SEQUENCE DESCRIPTION: SEQ ID NO:58:

```
AGTCAGTCGT GTCTATTGGG TTCAGCCAGT TCTGCTGGTG TATTCCCTTT AGACGGGTCA      60

ACATCAGTTC TGATCGGTGG ATAAGGGCTG GAGGAATGTG GCACTCTTCG GGGTGTGTTA     120

TAGCCTCCTG TCGCATACAC TGGTTGGGAC TGAGGAATGC AGCTCGCCTT TATGGCCGGG     180
```

GTTCGCCCAC GTTCGAGCTT AGGATGTTGA CAAAATGGCT TTAAACGACC CGTCTTGA          238

(2) INFORMATION FOR SEQ ID NO:59:

(i) SEQUENCE CHARACTERISTICS:
        (A) LENGTH: 236 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Filobasidium uniguttulatum (xi) SEQUENCE DESCRIPTION: SEQ ID NO:59:

AGTCAGTCGT GCTCAATGGA CTCAGCCGTT CTGCGGTGTA TTTCCATTGG GTGGGGTCAA          60

CATCAGTTTT GATCGCTGGA TAAAGGCAGG AGGAATGTAG CACCCCCGGG TGAACTTATA          120

GCCTCTTGTC ACATACAGTG GTTGGGACTG AGGAACGCAG CATGCCTTTA TGGCCGGGAT          180

TCGTCCACGT ACATGCTTAG GATGTTGACA TAATGGCTTT AAACGACCCG TCTTGA             236

(2) INFORMATION FOR SEQ ID NO:60:

(i) SEQUENCE CHARACTERISTICS:
        (A) LENGTH: 204 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Geotrichum (xi) SEQUENCE DESCRIPTION: SEQ ID NO:60:

AATCAGACTT GGTGCTGTTG TTCAACTRTG TTTCGGCATA GTGTACTCAG CAGTACTAGG          60

CCAAGGTGGG GTGTTTGGGA GTGAAAAAGA GTAGGAACG TAACTCTTCG GAGTGTTATA          120

GCCTACTTTC ATAGCTCCTC AGGCGCCTCA GGACTGCGCT TCGGCAAGGA CCTTGGCATA          180

ATGATTCTAT ACCGCCCGTC TTGA                                                204

(2) INFORMATION FOR SEQ ID NO:61:

(i) SEQUENCE CHARACTERISTICS:
        (A) LENGTH: 214 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Histoplasm capsulatum (xi) SEQUENCE DESCRIPTION: SEQ ID NO:61:

GAYCAGAGTC GGCCGYGGGG GTTCAGCGGG CATTCGTTGC CCGTGCAATC CCCCGCGGCC 60

GGGCCAGCGT CGGTTTCGAC GGCCGGTCAA AGGCCCCCGG AATGTGTCGC CTCTCGGGGC 120

GTCTTATAGC CGGGGGTGCA ATGCGGCCAG TCGGGACCGA GGAACGCGCT CCGGCACGGA 180

CGCTGGCTTA ATGGTCGTCA GCGACCCGTC TTGA 214

(2) INFORMATION FOR SEQ ID NO:62:

(i) SEQUENCE CHARACTERISTICS:
(A) LENGTH: 215 base pairs (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Malbranchea (xi) SEQUENCE DESCRIPTION: SEQ ID NO:62:

```
AGACAGACTC GAGCGCGGGG GCTCAGCGGG TATTGTTATG CCCGTGCACT CCCCCGCGCC      60
CGGGCCAGCA TCAGTTTTGG CGGCCGGTCA AAGGCCCTTG GAATGTATCG TCCTCCGGGA     120
CGTCTTATAG CCAAGGGTGC AATGCGGCCA GCCGGGACTG AGGAACGCGC TTCGGCACGG     180
ATGCTGGCGT AATGGCTGTA AGCGGCCCGT CTTGA                                215
```

(2) INFORMATION FOR SEQ ID NO:63:

(i) SEQUENCE CHARACTERISTICS:
        (A) LENGTH: 237 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Mucor (xi) SEQUENCE DESCRIPTION: SEQ ID NO:63:

```
AGCCAGACTG GTTTGACTGT AATCAACCTA GAATTCGTTC TGGGTGCACT TGCAGTCTAT      60
ACCTGCCAAC AACAGTTTGA TTTGGAGGAA AAAATTAGTA GGAATGTAGC CTCTCGAGGT     120
GTTATAGCCT ACTATCATAC TCTGGATTGG ACTGAGGAAC GCAGCGAATG CCWTTAGGCR     180
AGATTGCTGG GTGCTTTCGC TAATAAATGT TAGAATTTCT GCTTCGGGTG GTGCTAA       237
```

(2) INFORMATION FOR SEQ ID NO:64:

(i) SEQUENCE CHARACTERISTICS:
        (A) LENGTH: 209 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Paecilomyces (xi) SEQUENCE DESCRIPTION: SEQ ID NO:64:

```
GACCAGACTT GGGCCCGGTG GATCATCCAG CGTTCTCGCT GGTGCACTCC GCCGGGTTCA      60
GGCCAGCATC AGTTCGCCGC GGGGGAAAAA GGCTTCGGGA ACGTGGCTCC TACGGGAGTG     120
TTATAGCCCG TTGCATAATA CCCTGGGGCG GACTGAGGTT CGCGCTCCGC AAGGATGCTG     180
GCGTAATGGT CATCAGCGAC CCGTCTTGA                                      209
```

(2) INFORMATION FOR SEQ ID NO:65:

(i) SEQUENCE CHARACTERISTICS:
        (A) LENGTH: 199 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Penicillium (xi) SEQUENCE DESCRIPTION: SEQ ID NO:65:

```
GACCAGACTC GCCCACGGGG TTCAGCCGGC ATTCGTGCCG GTGTACTTCC CCGCGGGCGG      60

GCCAGCGTCG GTTTGGKCGG CCGGTCAAAG GCCCTCGGAA TRTAACGCCC CCCGGGGCGT     120

CTTATAGCCG AGGGTGCCAT GCGGCCAGCM CAGACCGAGG AACGCGCTTC GGCTCGGACG     180

CTGGCATAAT GGTCGTAAA                                                  199
```

(2) INFORMATION FOR SEQ ID NO:66:

(i) SEQUENCE CHARACTERISTICS:
        (A) LENGTH: 210 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Pseudallescheria boydii (xi) SEQUENCE DESCRIPTION: SEQ ID NO:66:

```
GACCAGACTT GTGCCCGTCG AATCAGCCGC CGCTCGTCGG CGGCGCACTT CGGCGGGCTC      60

AGGCCAGCAT CAGTTCGCTG CAGGGGGAGA AAGGCGATGG GAATGTGGCT CTTCGGAGTG     120

TTATAGCCCG CCGCGCAATA CCCCTCGGCG GACTGAGGAC CGCGCATCTG CAAGGATGCT     180

GGCGTAATGG TCGTCAGCGA CCCGTCTTGA                                      210
```

(2) INFORMATION FOR SEQ ID NO:67:

(i) SEQUENCE CHARACTERISTICS:
        (A) LENGTH: 244 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Rhizopus (NO:1)

(xi) SEQUENCE DESCRIPTION: SEQ ID NO:67:

```
AGCCAGACTG GCTTGTCTGT AATCAATCTA GGTTTCGTGC CTGGATGCAC TTGCAGACTA      60

TTTGCCTGCC AACGACAATT TTTTTTGAGT GTAAAAACTA TTGGAAATGT GGCCAATATT     120

TATTTATTGG TGTTATAGTC CTTTAGAAAA TACCTTGAAT TGGATTGAGG AACGCAGCGA     180

ATGCTTCTCT TTNGAGGCAA AGTCTTTTAT TGGGATTTAC GGATCAGACT GTGGCATTGT     240

CACA                                                                  244
```

(2) INFORMATION FOR SEQ ID NO:68:

(i) SEQUENCE CHARACTERISTICS:
        (A) LENGTH: 215 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Rhizopus (NO:2)

(xi) SEQUENCE DESCRIPTION: SEQ ID NO:68:

```
AGCCAGACTG GCTTGTCTGT AATCAATCTA GGCTTCGGCC TGGATGCACT TGCAGGCTAT      60

GCCTGCCAAC GACAATTTGA CTTGAGGGAA AAAACTAGGG GAAATGTGGC CCACTTGTGG     120
```

```
GTGTTATAGT CCCTTAGAAA ATACCTTGGG TTGGATTGAG GAACGCAGCG AATGCTTATT        180

GGCGAGTTTT CCAGGAAGGT TTTCTGAGGT ACTAC                                  215

(2) INFORMATION FOR SEQ ID NO:69:

(i) SEQUENCE CHARACTERISTICS:
        (A) LENGTH: 215 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Rhizopus (NO:3)

(xi) SEQUENCE DESCRIPTION: SEQ ID NO:69:

AGCCAGACTG GCTTGTCTGT AATCAGTCTA AGCTTCGGCT TGGATGCACT TGCAGGCTAT         60

GCCTGCCAAC GACAATTTGG CTTGAGGGAA AAAACTAAGG GAAATGTGGC CCATCCGTGG        120

GTGTTATAGT CCCTTAGAAA ATACCTTGGG CTGGATTGAG GTACGCAGCG AATGCTATTT        180

GGCGAGTTGG CTGGGAATAT TTTCTGAGGT GCTTT                                  215

(2) INFORMATION FOR SEQ ID NO:70:

(i) SEQUENCE CHARACTERISTICS:
        (A) LENGTH: 210 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Sporothrix (xi) SEQUENCE DESCRIPTION: SEQ ID NO:70:

GACCAGACTT GCGCCYCGCG GACCACCCGG CGTTCTCGCC GGTGCACTCT GCGKKGCGCA         60

GGCCAGCATC GGTTCTCCCA GGGGGACAAA GGCCGCGGGA ACGTAGCTCC TTCGGGAGTG        120

TTATAGCCCG CGGCGGCATG CCCCTGGGGG GACCGAGGAC CGCGCTTCGG CAAGGATGCT        180

GGCGTAATGG TCACCAGCGA ACCGTCTTGA                                        210

(2) INFORMATION FOR SEQ ID NO:71:

(i) SEQUENCE CHARACTERISTICS:
        (A) LENGTH: 208 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Scopulariopsis brevicaulis (xi) SEQUENCE DESCRIPTION: SEQ ID NO:71:

GACCAGACTT GCGCCCGTCG GATCAACCGT CGCTTGCGGC GGCGCACTCC GGCGGGCTCA         60

GGCCAGCATC AGTTCGTCCG GGGGGAGAAA GGCGGCGGGA ATGTGGCTCT TCGGAGTGTT        120

ATAGCCCGCC GTGTAATACC CTCGGGTGGA CTGAGGACCG CGCGTATGCA AGGATGCTGG        180

CGTAATGGTC GTCAGCGACC CGTCTTGA                                          208

(2) INFORMATION FOR SEQ ID NO:72:
```

(i) SEQUENCE CHARACTERISTICS:
    (A) LENGTH: 210 base pairs
    (B) TYPE: nucleic acid
    (C) STRANDEDNESS: single
    (D) TOPOLOGY: linear (ii) MOLECULE TYPE: DNA (genomic)

(vi) ORIGINAL SOURCE:
    (A) ORGANISM: Scopulariopsis brumptii (xi) SEQUENCE DESCRIPTION: SEQ ID NO:72:

```
GACCAGACTC GCGCCCGTCG GATCAGCCGT CGCTCGTCGG CGGCGCACTC CGGCGGGCTC    60

GGGCCAGCAT CAGTTCGCCT CGGGGGGAGA AAGGCGGCGG GAATGTGGCT CTACGGAGTG   120

TTATAGCCCG CCGCGTAATA CCCCCGGGCG GACTGAGGAC CGCGCGTATG CAAGGATGCT   180

GGCGTAATGG TCGTCAGCGA CCCGTCTTGA                                    210
```

(2) INFORMATION FOR SEQ ID NO:73:

(i) SEQUENCE CHARACTERISTICS:
        (A) LENGTH: 214 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Saccharomyces cerevisiae (xi) SEQUENCE DESCRIPTION: SEQ ID NO:73:

```
GATCAGACAT GGTGTTTTGT GCCCTCTGCT CCTTGTGGGT AGGGGAATCT CGCATTTCAC    60

TGGGCCAGCA TCAGTTTTGG TGGCAGGATA AATCCATAGG AATGTAGCTT GCCTCGGTAA   120

GTATTATAGC CTGTGGGAAT ACTGCCAGCT GGGACTGAGG ACTGCGACGT AAGTCAAGGA   180

TGCTGGCATA ATGGTTATAT GCCGCCCGTC TTGA                               214
```

(2) INFORMATION FOR SEQ ID NO:74:

(i) SEQUENCE CHARACTERISTICS:
        (A) LENGTH: 236 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Trichosporon beigelii (xi) SEQUENCE DESCRIPTION: SEQ ID NO:74:

```
AGTCAGTCGT GTTCTTTGGA TTCAGCCAGT TCTGCTGGTC TACTTCCTTG GAACGGGTCA    60

ACATCAGTTT TGTCCGGTGG ATAAAGGTAG TAGGAATGTG ACTTCTCCGG AAGTGTTATA   120

GCCTATTATC ACATACACTG GGTGAGACTG AGGACTGCAG CTCGCCTTTA TGGCCGGCCT   180

TCGGGCACGT TCGAGCTTAG GATGTTGACA TAATGGCTTT AAACGACCCG TCTTGA       236
```

(2) INFORMATION FOR SEQ ID NO:75:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

-continued (xi) SEQUENCE DESCRIPTION: SEQ ID NO:75:

ATCAATAAGC GGAGGAAAAG     20

(2) INFORMATION FOR SEQ ID NO:76:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:76:

CTCTGGCTTC ACCCTATTC     19

(2) INFORMATION FOR SEQ ID NO:77:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:77:

TCCCTTTCAA CAATTTCACG     20

(2) INFORMATION FOR SEQ ID NO:78:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:78:

GGTCCGTGTT TCAAGACGG     19